US007642290B2

(12) United States Patent
Kaplan

(10) Patent No.: US 7,642,290 B2
(45) Date of Patent: Jan. 5, 2010

(54) COMPOUNDS FOR USE IN THE TREATMENT OF AUTOIMMUNE DISEASES, IMMUNO-ALLERGICAL DISEASES AND ORGAN OR TISSUE TRANSPLANTATION REJECTION

(75) Inventor: Eliahu Kaplan, Ramat-HaSharon (IL)

(73) Assignee: Novaremed Limited, Tel-Aviv (IL)

( * ) Notice: Subject to any disclaimer, the term of this patent is extended or adjusted under 35 U.S.C. 154(b) by 75 days.

(21) Appl. No.: 10/530,116

(22) PCT Filed: Oct. 1, 2003

(86) PCT No.: PCT/IB03/04993

§ 371 (c)(1),
(2), (4) Date: Nov. 29, 2005

(87) PCT Pub. No.: WO2004/031129

PCT Pub. Date: Apr. 15, 2004

(65) Prior Publication Data

US 2006/0135620 A1     Jun. 22, 2006

Related U.S. Application Data

(60) Provisional application No. 60/415,508, filed on Oct. 3, 2002.

(51) Int. Cl.
*A61K 31/165* (2006.01)
*C07C 233/16* (2006.01)
*C07C 233/23* (2006.01)
(52) U.S. Cl. ..................................... 514/617; 564/123
(58) Field of Classification Search .................. 514/617; 564/123
See application file for complete search history.

(56) References Cited

U.S. PATENT DOCUMENTS

| 4,766,106 A * | 8/1988 | Katre et al. .................... 514/12 |
| 4,908,322 A | 3/1990 | Jacobson et al. ............. 436/111 |
| 2006/0148874 A1 * | 7/2006 | Kaplan et al. ............... 514/396 |

FOREIGN PATENT DOCUMENTS

WO    WO 02/46176 A1    6/2002

OTHER PUBLICATIONS

Greenwald et al. Journal of Organic Chemistry, 1995, vol. 60, pp. 331-336.*
Takeuchi et al., Abstract of Comparative Biochemistry and physiology, C: Comparative Pharmacology (1983), 75C(2), 329-35.*
Adamczyk et al., "Stereoselective *Pseudomonas cepacia* lipase mediated synthesis of α-hydroxyamides", *Tetrahedron: Asymmetry*, 8(15):2509-2512, (1997).
Arutyunyan et al., "Synthesis of Pseudosparsomycins", *Pharm. Chem. J.*, (English Translation), 23(10):837-840 (1989).

Braun et al., "New Oxidative Transformations of Phenolic and Indolic Oxazolines: An Avenue to Useful Azaspirocyclic Building Blocks", *J. Org. Chem.*, 65(14):4397-4408 (2000).
Bussolari et al., "Parallel synthesis of 2-alkoxy and 2-acyloxyphenylpropyl amides and amines using dihydrocoumarins as versatile synthons. Application of a novel resin quench-capture method", *Tetrahedron Lett.*, 40(7):1241-1244 (1999).
Caldirola et al., "New prenylamine-analogues: investigations of their influence on calcium-dependent biological systems", *Eur. J. Med. Chem.*, 28:555-568 (1993).
Clark et al., "Some Substituted Phenethyl and 3-Phenylpropyl Styryl Ketones and the Corresponding Saturated Ketones", *J. Chem. Soc.*, pp. 126-130 (1962).
Davyt et al., "A new Indole Derivative from the Red Alga *Chondria atropurpurea*. Isolation, Structure Determination, and Anthelmintic Activity", *J. Nat. Prod.*, 61(12):1560-1563 (1998).
Detert et al., "Cationic amphiphiles with G-protein-stimulatory activity: Studies on the role of the basic domain in the activation process" *Pharmazie*, 51(2):67-72 (1996).
Dumont et al., "Note on Attempts to Prepare Ring-B Homomorphinan-6-ones by *Grewe* Cyclization from Octahydro-1-phenethylisoquinolines", *Helvetica Chimica Acta*, 68(8):2128-2131 (1985).
Glennon et al., "Influence of Amine Substituents on 5-HT2A versus 5-HT2C Binding of Phenylalkyl- and Indolylalkylamines", *J. Med. Chem.*, 37(13):1929-1935 (1994).
Heilbron et al., "CLXXVII.-Styrylpyrylium Salts. Part XIII. The Reactivity of Methyl β-Phenylethyl and Methyl γ-Phenylpropyl Ketones", *J. Chem. Soc.*, pp. 1336-1342 (1931).
Herbert et al., "The Biosynthesis of *Sceletium* Alkaloids in *Sceletium Subvelutinum* L. Bolus", *Tetrahedron*, 46(20):7105-7118 (1990).
Horii et al., "Syntheses and Pharmacological Properties of 2- and 3-Aralkyltetrahydro-1,3-oxazines", *Chem. Pharm. Bull.*, 13(10):1151-1159 (1965).
Kamenecka et al., "Construction of Substituted Cyclohexanones by Reductive Cyclization of 7-Oxo-2,8-alkadienyl Esters", *Organic Lett.*, 4(1):79-82 (2002).
Kunishima et al., "Synthesis and Characterization of 4-(4,6-Dimethxy-1,3,5-triazin-2-yl)-4-methylmorpholinium Chloride", *Tetrahedron Lett.*, 40:5327-5330 (1999).
Le Blanc et al., "New Access to Spiranic β-Lactams", *Tetrahedron Lett.*, 33(15):1993-1996 (1992).
Luly et al., "Modified Peptides which Display Potent and Specific Inhibition of Human Renin", *Biochem. Biophys. Res. Commun.*, 143(1):44-51 (1987).

(Continued)

*Primary Examiner*—Yong Chu
(74) *Attorney, Agent, or Firm*—Ivor R. Elrifi; Mintz, Levin, Cohn, Ferris, Glovsky and Popeo, P.C.

(57) ABSTRACT

The present invention provides compounds, pharmaceutical compositions and methods for treating, immuno-allergical diseases, autoimmune diseases, and organ or tissue rejection following transplantation.

36 Claims, 18 Drawing Sheets

OTHER PUBLICATIONS

Nivlet et al., "Reductive Opening of Cyclopropylogous α-Hydroxy Aldehydes and Ketones by Samarium(II) Iodide", *Tetrahedron Lett.*, 39:2115-2118 (1998).

Obora et al., "Palladium Complex Catalyzed Acylation of Allylic Esters with Acylsilanes", *J. Am. Chem. Soc.*, 123(43):10489-10493 (2001).

Ochiai et al., "Triphenylphosphine-mediated olefination of aldehydes with (Z)-(2-acetoxyalk-1-enyl)phenyl-$\lambda^3$-iodanes", *Chem. Commun.*, 13:1157-1158 (2000).

Paul et al., "Condensation de quelques éthers vinyliques hétérocycliques avec l'acroléine et ses homologues", *Bull. Soc. Chim. Fr.*, in French, pp. 672-678 (1954).

Rao et al., "Synthetic Studies in Polycyclic Systems: Part VI*—Syntheses of 3- Phenyl-, I-Methyl-3- phenyl- & I,3-Diphenyl-phenanthrenes", *Ind. J. Chem.*, 14B:38-40 (1976).

Takeuchi et al., "Inhibitory effects of derivatives of tyrosine and tryptophan on mollusca giant neurons", *Neurosci.*, 9(1):122-123 (1983).

Tamiz et al., "Structure-Activity Relationships for a Series of Bis(phenylalkyl)amines: Potent Subtype-Selective Inhibitors of N-Methyl-D-aspartate Receptors", *J. Med. Chem.*, 41(18):3499-3506 (1998).

Umino et al., "Sodium Acyloxyborohydride as New Reducing Agents. I. Reduction of Carboxamides to the corresponding Amines", *Tetrahedron Lett.*, No. 10, pp. 763-766 (1976).

Yasuma et al., "Synthesis of Peptide Aledehyde Derivatives as Selective Inhibitors of Human Cathepsin L and their Inhibitory Effect on Bone Resorption", *J. Med. Chem.*, 41(22):4301-4308 (1998).

Chemical Abstracts Service, JP 52 036606 A2, "Process for Preparation of Amino Compounds", Tanabe Seiyaku Co. Ltd., Mar. 22, 1977.

* cited by examiner

COMPOUNDS FOR USE IN THE TREATMENT OF AUTOIMMUNE DISEASES, IMMUNO-ALLERGICAL DISEASES AND ORGAN OR TISSUE TRANSPLANTATION REJECTION

RELATED APPLICATIONS

This application is a national stage application, filed under 35 U.S.C. § 371, of International Application No. PCT/IB2003/004993, filed on Oct. 1, 2003, which claims priority from U.S. application Ser. No. 60/415,508, filed Oct. 3, 2002.

FIELD OF THE INVENTION

The present invention relates to novel compounds useful in the treatment of autoimmune diseases, immuno-allergical disease and organ or tissue transplantation rejection.

BACKGROUND OF THE INVENTION

Diseases of the immune systems pose a major threat due to the potentially devastating effects that such diseases have on humanity. One class of diseases related to the immune system are immuno-allergical diseases. Immuno-allergical diseases are a major cause of concern, and much research is being conducted in order to develop potent compounds that will be effective in treating such diseases. Allergy is a state of hypersensitivity induced by exposure to a particular antigen (allergen) resulting in harmful immunologic reaction on subsequent exposures. An example of an immuno-allergical disease is allergic rhinitis (hay fever). Allergic rhinitis is a common immuno-allergic condition that affects one in every five Americans. Over one billion dollars is spent each year in the U.S. to treat this condition. Sneezing, nasal congestion, and eye irritation are some of the symptoms of allergic rhinitis. Another example of an immuno-allergical disease is bronchial asthma—a breathing problem that results from spasm (bronchospasm) of the muscles surrounding the walls of the lung airways (bronchi). Allergic asthma is the most common type of asthma, typically first appearing in childhood.

Another example of an immuno-allergical disease is psoriasis, which is a chronic skin disease characterized by scaling and inflammation, and it affects 1.5 to 2 percent of the United States population, or almost 5 million people. It occurs in all age groups and about equally in men and women. People with psoriasis may suffer discomfort, restricted motion of joints, and emotional distress.

Another type of immuno-allergical disease is Crohn's disease, which is a chronic inflammatory disease of the intestines. It primarily causes ulceration in the small and large intestines but can affect the digestive system anywhere between the mouth and the anus. The disease is found in equal frequency in men and women, and it usually affects young patients in their teens or early twenties. Once the disease begins, it tends to be a chronic, recurrent condition with periods of remission and disease exacerbation.

A third class of diseases related to the immune system are autoimmune diseases. Autoimmune diseases are illnesses that occur when the body's tissues are attacked by its own immune system. The immune system is a complex organization within the body that is designed normally to seek and destroy invaders of the body, particularly infections. Patients with these diseases have unusual antibodies in their blood that target their own body tissues. An example of an autoimmune disease is systemic lupus erythematosus. Lupus is a chronic inflammatory condition, caused by autoimmune disease, which causes disease of the skin, heart, lungs, kidneys, joints, and nervous system. When internal organs are involved, the condition is called systemic lupus erythematosus. Another type of an autoimmune disease is autoimmune thyroiditis, which is an autoimmune disease of the thyroid. Another type of autoimmune disease is rheumatoid arthritis, which causes chronic inflammation of the joints, the tissue around the joints, as well as other organs in the body.

Another example of an autoimmune system is experimental autoimmune enoephalomyelitis (EAE). EAE is an inflammatory condition of the central nervous system, which is the murine equivalent to multiple sclerosis.

A forth class of conditions related to the immune system is organ or tissue rejection following transplantation. Organ or tissue rejection is a major complication occurring in patients who have undergone transplantation. For example, chronic graft-versus-host disease (cGvHD), a major complication occurring in patients post-allogeneic bone marrow transplantation, is believed to be the result of an autoimmune-like process mediated by immunocompetent T-cells. Chronic GvHD often results in sclerodermoid-fibrotic skin lesions [see, e.g., Chosidow et al., Sclerodermatous chronic graft-versus-host disease analysis of seven cases. J Am Acad Dermatol 26:49-53, 1992]. Other examples of organ or tissue rejection following transplantation include skin graft rejection and cardiac graft rejection.

Autoimmune diseases and immuno-allergical diseases pose a major problem to society. Organ or tissue rejection following transplantation presents another problem that severely limits the use and application of tissue and organ transplantation in medicine.

SUMMARY OF THE INVENTION

The present invention relates to novel compounds useful in the treatment, prevention, and control of immuno-allergical diseases, autoimmune diseases and organ or tissue transplantation rejection following transplantation.

The present invention provides a compound represented by the structure of formula I

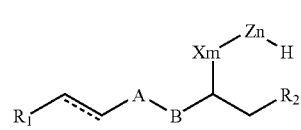

wherein
the dotted line represents a single or a double bond;
In one embodiment, $R_1$ and $R_2$ are the same or different, and independently of each other represent —$CH_2OH$, —$CH_2OR_4$, —$CH(OH)CH_3$, —$CH(OR_4)CH_3$, or a group represented by the formula

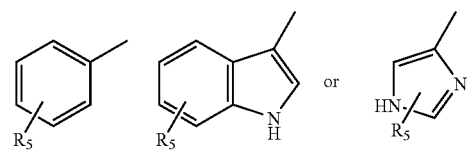

where $R_4$ is a linear or branched $C_1$-$C_4$ alkyl; $R_5$ is H, OH or $OR_6$ (where $R_6$ is a linear or branched $C_1$-$C_4$ alkyl); and A-B is a group represented by the formula:

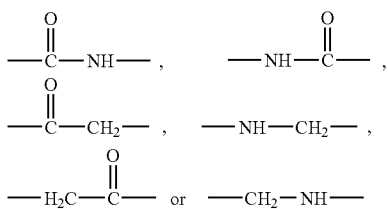

In various embodiments, X is O, —CH$_2$O, —CH$_2$CH$_2$O, —CH(CH$_3$)CH$_2$O, or —CH$_2$CH(CH$_3$)O, and Z is —CH$_2$CH$_2$O, —CH(CH$_3$)CH$_2$O, or —CH$_2$CH(CH$_3$)O.
m is an integer of 0 or 1; and n is an integer of 0-50.
In another embodiment, n is an integer from 1-100.
In another embodiment, n is an integer from 1-200.
In yet another embodiment, n is an integer from 1-500.
In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.
In another embodiment, the present invention provides the salts or hydrates of the compound presented by the structure of formula I.
In one embodiment, R$_1$ is —CH$_2$OH, —CH$_2$OR$_4$, —CH(OH)CH$_3$, or —CH(OR$_4$)CH$_3$. In another embodiment, R$_1$ is

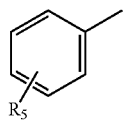

where R$_5$ is H or OH. In another embodiment, R$_1$ is phenyl. In another embodiment, R$_1$ is

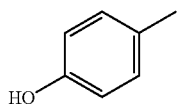

In one embodiment, R$_2$ is —CH$_2$OH, —CH$_2$OR$_4$, —CH(OH)CH$_3$, or —H(OR$_4$)CH$_3$. In another embodiment, R$_2$ is

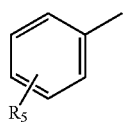

where R$_5$ is H or OH. In another embodiment, R$_2$ is phenyl. In another embodiment, R$_2$ is

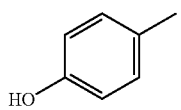

In another aspect, the present invention provides a compound represented by the structure of formula II

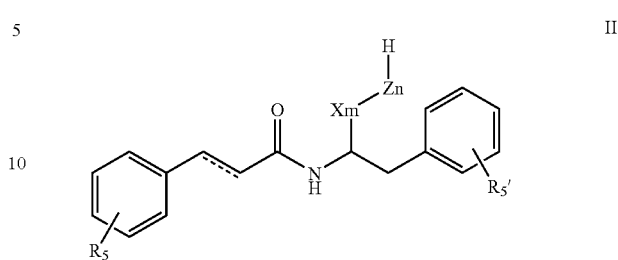

where
the dotted line represents a single or a double bond;
R$_5$ and R$_5$' are, independently of each other, H, OH or OR$_6$ where R$_6$ is a linear or branched C$_1$-C$_4$ alkyl.
In various embodiments, X is O, —CH$_2$O, —CH$_2$CH$_2$O, —CH(CH$_3$)CH$_2$O, or —CH$_2$CH(CH$_3$)O; and Z is —CH$_2$CH$_2$O, —CH(CH$_3$)CH$_2$O, or —CH$_2$CH(CH$_3$)O.
m is an integer of 0 or 1; and n is an integer of 0-50.
In another embodiment, n is an integer from 1-100.
In another embodiment, n is an integer from 1-200.
In yet another embodiment, n is an integer from 1-500.
In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.
In another embodiment, the present invention provides the salts or hydrates of the compound presented by the structure of formula II.
In one embodiment, X is —CH$_2$O.
In one embodiment, m is 0. In another embodiment, m is 1.
In addition, the present invention provides a compound represented by the structure of formula III

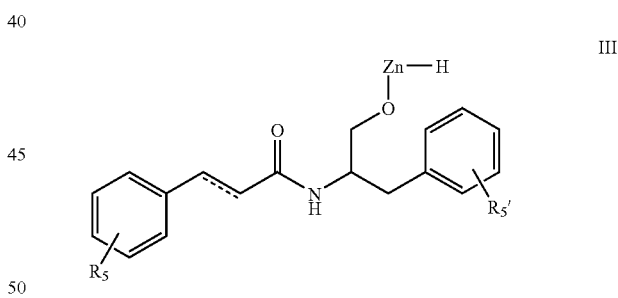

where the dotted line represents a single or a double bond; R$_5$ and R$_5$' are, independently of each other, H, OH or OR$_6$ (where R$_6$ is a linear or branched C$_1$-C$_4$ alkyl), Z is —CH$_2$CH$_2$O, —CH(CH$_3$)CH$_2$O, or —CH$_2$CH(CH$_3$)O, and n is an integer of 0-50.
In another embodiment, n is an integer from 1-100.
In another embodiment, n is an integer from 1-200.
In yet another embodiment, n is an integer from 1-500.
In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.
In another embodiment, the present invention provides the salts or hydrates of the compound presented by the structure of formula III.

In one embodiment, Z is —CH(CH$_3$)CH$_2$O.

In addition, the present invention provides a compound represented by the structure of formula IV

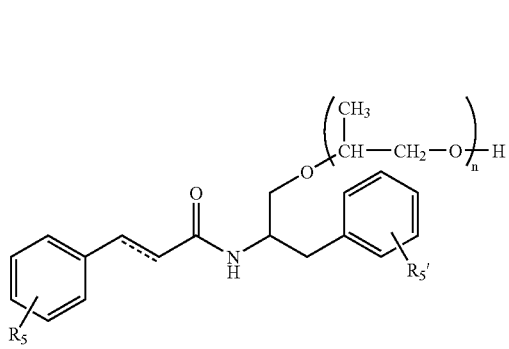

where the dotted line represents a single or a double bond;
R$_5$ and R$_5$' are, independently of each other, H, OH or OR$_6$ (where R$_6$ is a linear or branched C$_1$-C$_4$ alkyl); and
Z is —CH$_2$CH$_2$O, —CH(CH$_3$)CH$_2$O, or —CH$_2$CH(CH$_3$)O.
n is an integer of 0-50.
In another embodiment, n is an integer from 1-100.
In another embodiment, n is an integer from 1-200.
In yet another embodiment, n is an integer from 1-500.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

In another embodiment, the present invention provides the salts or hydrates of the compound presented by the structure of formula IV.

In one embodiment, R$_5$ is H. In another embodiment, R$_5$ is OH.

In one embodiment, R$_5$' is H. In another embodiment, R$_5$' is OH.

In one embodiment, n is an integer of 1-20. In another embodiment, n is an integer of 10-20. In another embodiment, n is 17.

In addition, the invention provides a compound of Formula A:

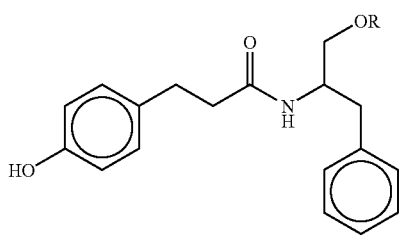

Formula A wherein R is a polyalkylene glycol polymer having n units, where n is an integer from 1-100.

In one embodiment, the polyalkylene glycol polymer is polyisopropylene glycol.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

In addition, the invention provides a compound of Formula B:

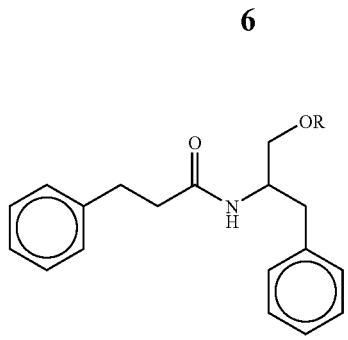

Formula B wherein R is a polyalkylene glycol polymer having n units, where n is an integer from 1-100.

In one embodiment, the polyalkylene glycol polymer is polyisopropylene glycol.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

In addition, the invention provides a compound of Formula C:

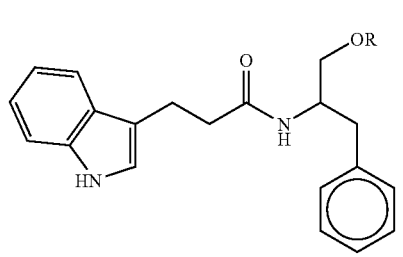

Formula C wherein R is a polyalkylene glycol polymer having n units, where n is an integer from 1-100.

In one embodiment, the polyalkylene glycol polymer is polyisopropylene glycol.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

In addition, the invention provides a compound of Formula D:

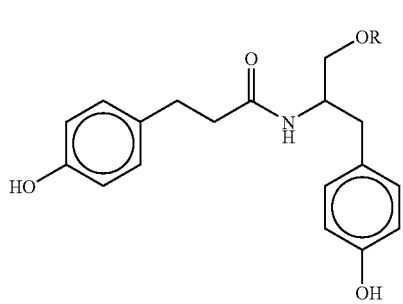

Formula D wherein R is a polyalkylene glycol polymer having n units, where n is an integer from 1-100.

In one embodiment, the polyalkylene glycol polymer is polyisopropylene glycol.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

In addition, the invention provides a compound of Formula E:

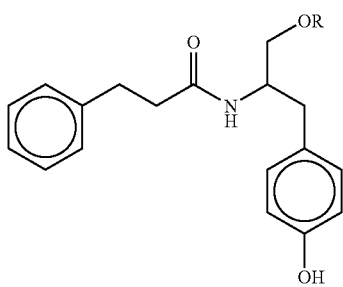

Formula E wherein R is a polyalkylene glycol polymer having n units, where n is an integer from 1-100.

In one embodiment, the polyalkylene glycol polymer is polyisopropylene glycol.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

In addition, the invention provides a compound of Formula F:

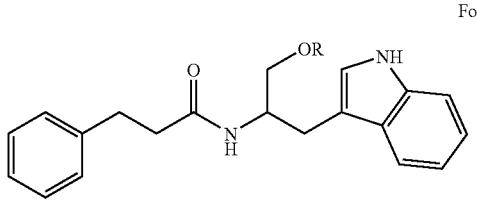

Formula F wherein R is a polyalkylene glycol polymer having n units, where n is an integer from 1-100.

In one embodiment, the polyalkylene glycol polymer is polyisopropylene glycol.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

Furthermore, in one embodiment, the present invention provides a composition comprising one or more compounds of formula I, II, III, IV, VII, A, B, C, D, E, or F. In another embodiment, the present invention provides a pharmaceutical composition comprising as an active ingredient one or more compounds of formula I, II, III, IV, VII, A, B, C, D, E, or F, together with one or more pharmaceutically acceptable excipients or adjuvants.

Furthermore, in one embodiment, the present invention provides a method for the treatment, prevention and control of immuno-allergical diseases in human as well as veterinary applications, which comprises administrating one or more compounds of formula I, II, III, IV, VII, A, B, C, D, E, or F and/or a pharmaceutical composition comprising one or more compounds of formula I, II, III, IV, VII, A, B, C, D, E, or F. In one embodiment, the immuno-allergical disease is bronchial asthma, allergic rhinitis, psoriasis or Crohn's disease.

Furthermore, in one embodiment, the present invention provides a method for the treatment, prevention and control of autoimmune diseases in human as well as veterinary applications, which comprises administrating one or more compounds of formula I, II, III, IV, VII, A, B, C, D, E, or F and/or a pharmaceutical composition comprising one or more compounds of formula I, II, III, IV, VII, A, B, C, D, E, or F. In one embodiment, the autoimmune disease is systemic lupus erythematosus, autoimmune thyroiditis, rheumatoid arthritis, diabetes, multiple sclerosis and experimental autoimmune encephalomyelitis.

Furthermore, in one embodiment, the present invention provides a method for the treatment, prevention and control of organ or tissue transplantation rejection in human as well as veterinary applications, which comprises administrating one or more compounds of formula I, II, III, IV, VII, A, B, C, D, E, or F and/or a pharmaceutical composition comprising one or more compounds of formula I, II, III, IV, VII, A, B, C, D, E, or F. In one embodiment, the organ or tissue transplantation rejection is kidney rejection, bone marrow rejection, skin graft rejection, cardiac graft rejection or chronic-graft-versus-host disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

DETAILED DESCRIPTION OF THE INVENTION

Figure 1:
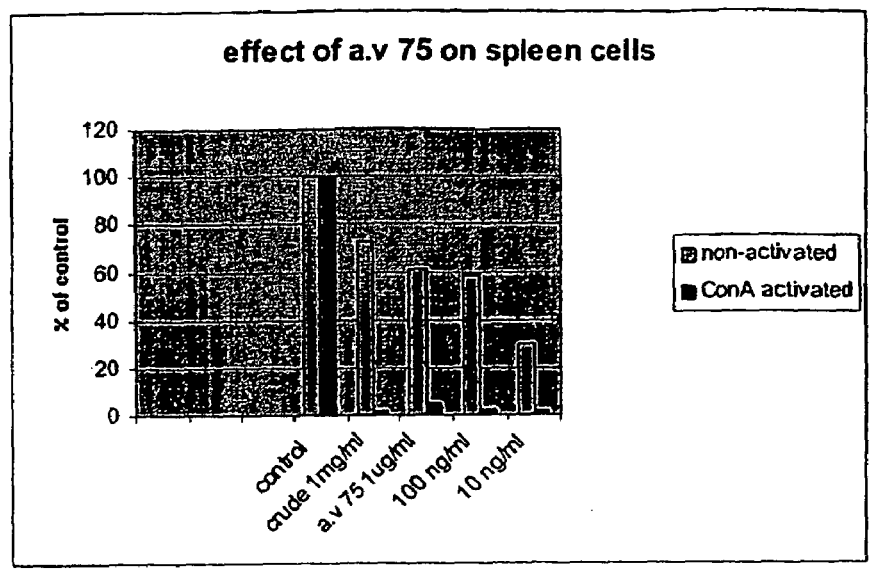
FIG. 1 is a bar graph depicting the effect of AV 75 on spleen cells±ConA.

The present invention provides novel compounds and pharmaceutical compositions useful in the treatment of immuno-allergical diseases, autoimmune diseases and organ or tissue transplantation rejection. The present invention further provides a method for the treatment, prevention and control of immuno-allergical diseases, autoimmune diseases, and organ or issue transplantation rejection comprising administering to a subject one or more of the compounds represented by the structure of formula I, II, III, IV, VII, A, B, C, D, E, or F.

In one embodiment, the present invention provides a compound represented by the structure of formula I:

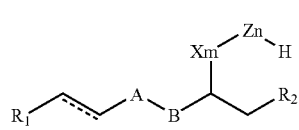

wherein $R_1$ and $R_2$ are the same or different, and independently of each other represent —$CH_2OH$, —$CH_2OR_4$, —$CH(OH)CH_3$, —$CH(OR_4)CH_3$, or a group represented by the formula

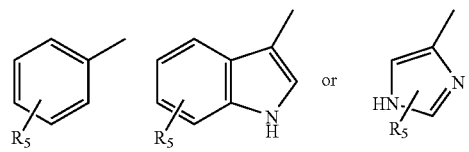

wherein $R_4$ is a linear or branched $C_1$-$C_4$ alkyl;

$R_5$ is H, OH or $OR_6$ wherein $R_6$ is a linear or branched $C_1$-$C_4$ alkyl;

A-B is a group represented by the formula:

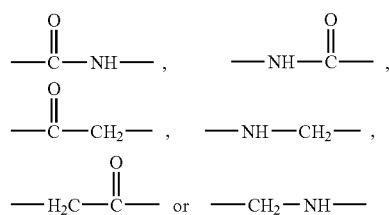

X is O, —$CH_2O$, —$CH_2CH_2O$, —$CH(CH_3)CH_2O$, or —$CH_2CH(CH_3)O$;

Z is —$CH_2CH_2O$, —$CH(CH_3)CH_2O$, or —$CH_2CH(CH_3)O$;

m is an integer of 0 or 1; and n is an integer of 0-50;

and salts or hydrates thereof.

In another embodiment, n is an integer from 1-100.

In another embodiment, n is an integer from 1-200.

In yet another embodiment, n is an integer from 1-500.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

In another embodiment, the present invention further provides a compound represented by the structure of formula II:

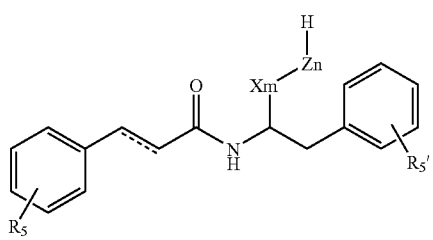

II wherein $R_5$ and $R_5'$ are independently of each other H, OH or $OR_6$ wherein $R_6$ is a linear or branched $C_1$-$C_4$ alkyl;

X is O, —$CH_2O$, —$CH_2CH_2O$, —$CH(CH_3)CH_2O$, or —$CH_2CH(CH_3)O$;

Z is —$CH_2CH_2O$, —$CH(CH_3)CH_2O$, or —$CH_2CH(CH_3)O$;

m is an integer of 0 or 1; and n is an integer of 0-50;

and salts or hydrates thereof.

In another embodiment, n is an integer from 1-100.

In another embodiment, n is an integer from 1-200.

In yet another embodiment, n is an integer from 1-500.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

In another embodiment, the present invention provides a compound represented by the structure of formula III:

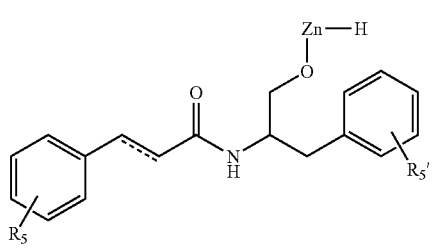

III wherein $R_5$ and $R_5'$ are independently of each other H, OH or $OR_6$ wherein $R_6$ is a linear or branched $C_1$-$C_4$ alkyl;

Z is —$CH_2CH_2O$, —$CH(CH_3)CH_2O$, or —$CH_2CH(CH_3)O$;

n is an integer of 0-50;

and salts or hydrates thereof.

In another embodiment, n is an integer from 1-100.

In another embodiment, n is an integer from 1-200.

In yet another embodiment, n is an integer from 1-500.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

The present invention provides a compound represented by the structure of formula IV:

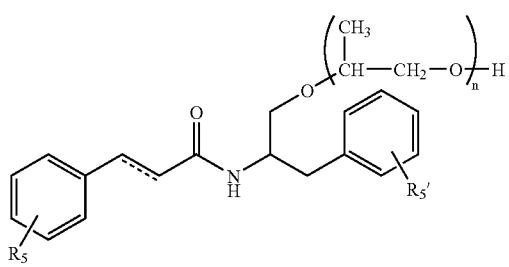

IV

Wherein $R_5$ and $R_5'$ are independently of each other H, OH or $OR_6$ wherein $R_6$ is a linear or branched $C_1$-$C_4$ alkyl;

n is an integer of 0-50;

and salts or hydrates thereof.

In another embodiment, n is an integer from 1-100.

In another embodiment, n is an integer from 1-200.

In yet another embodiment, n is an integer from 1-500.

In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

As contemplated herein, an "alkyl" group refers to a saturated aliphatic hydrocarbon, including straight-chain, branched-chain and cyclic alkyl groups. In one embodiment, the alkyl group has 1-4 carbons. In another embodiment, the alkyl group is a methyl group. In another embodiment, the alkyl group is an ethyl group. In another embodiment, the alkyl group is a propyl group. In another embodiment, the alkyl group is a butyl group. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

In one embodiment, $R_1$ and $R_2$ are the same or different in the compounds of the invention, and, independently of each other, represent —$CH_2OH$, —$CH_2OR_4$, —$CH(OH)CH_3$, —$CH(OR_4)CH_3$, or a group represented by the formula:

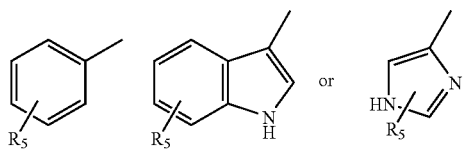

In one embodiment, $R_4$ is a linear or branched $C_1$-$C_4$ alkyl.

In one embodiment, A-B is a group represented by the formula:

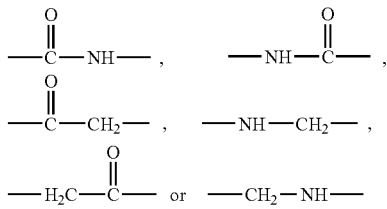

In one embodiment, X is O, —CH$_2$O, —CH$_2$CH$_2$O, —CH(CH$_3$)CH$_2$O, or —CH$_2$CH(CH$_3$)O.

In one embodiment, m is an integer of 0 or 1.

In one embodiment, Z is —CH$_2$CH$_2$O, —CH(CH$_3$)CH$_2$O, or —CH$_2$CH(CH$_3$)O.

In one embodiment, n is an integer of 0-50. In another embodiment, n is an integer of 1-20. In another embodiment, n is an integer of 10-20. In another embodiment, n is 17. In various other embodiments, n is 7, 12, or 34. In other embodiments, n is an integer from 1-100, an integer from 1-200, an integer from 1-500. In another embodiment, n is an integer from 5-75. For example, n can be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is, 7, 12, 17, 34 or 69.

In one embodiment, R$_5$ is H, OH or OR$_6$.

In one embodiment, R$_5$' is H, OH or OR$_6$.

In one embodiment, R$_6$ is a linear or branched C$_1$-C$_4$ alkyl.

The synthetic methodologies for obtaining the compounds are disclosed in detail in the Examples section, below. However, it should be apparent to a person skilled in the art that the compounds of the present invention can be prepared by any feasible synthetic method and that the syntheses set forth in the Experimental Details Section are in no way limiting. Various synthetic methods for the preparation of these compounds will be known to a person skilled in the art. Compounds of the invention may be further modified as allowed by the rules of chemistry. Such modifications include the addition of various substituents (e.g., hydroxylation, carboxylation, methylation, etc.), generation of enantiomers, creation of acid- or base-addition salts, and the like. Other modifications include adding polyalkylene glycol polymers.

The compounds of the invention may be synthesized as polyalkylene glycol (PAG) conjugates. Typical polymers used for conjugation include poly(ethylene glycol) (PEG), also known as or poly(ethylene oxide) (PEO) and polypropylene glycol (including poly isopropylene glycol). These conjugates are often used to enhance solubility and stability and to prolong the blood circulation half-life of molecules.

In its most common form, a polyalkylene glycol (PAG), such as PEG is a linear polymer terminated at each end with hydroxyl groups:

HO—CH$_2$CH$_2$O—(CH$_2$CH$_2$O)$_n$—CH$_2$CH$_2$—OH.

The above polymer, alpha-, omega-dihydroxylpoly(ethylene glycol), can also be represented as HO-PEG-OH, where it is understood that the -PEG-symbol represents the following structural unit:

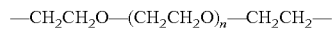
—CH$_2$CH$_2$O—(CH$_2$CH$_2$O)$_n$—CH$_2$CH$_2$— where n typically ranges from about 4 to about 10,000. PEG is commonly used as methoxy-PEG-OH, or mPEG, in which one terminus is the relatively inert methoxy group, while the other terminus is a hydroxyl group that is subject to ready chemical modification. Additionally, random or block copolymers of different alkylene oxides (e.g., ethylene oxide and propylene oxide) that are closely related to PEG in their chemistry can be substituted for PEG in many of its applications.

PAGs are polymers which typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995).

Polyalkylated compounds of the invention typically contain between 1 and 500 monomeric units. Other PAG compounds of the invention contain between 1 and 200 monomeric units. Still other PAG compounds of the invention contain between 1 and 100 monomeric units. For example, the polymer may contain 1, 10, 20, 30, 40, 50, 55, 60, 65, 70, 75, 80, 85, 90, 95, or 100 monomeric units. Some compounds of the invention contain polymers which include between 5 and 75 or between 1 and 50 monomeric units. For example, the polymer may contain 2, 3, 5, 6, 7, 8, 10, 11, 12, 13, 15, 16, 17, 18, 20, 25, 30, 33, 34, 35, 40, 45, 50, 60, 65, 68, 69, 70, or 75 monomeric units. Preferably, n is, 7, 12, 17, 34 or 69. The polymers can be linear or branched.

It is to be understood that compounds which have been modified by the addition of a PAG moiety may include a mixture of polymers which have a varying number of monomeric units. Typically, the synthesis of a PAG-modified compound (e.g., a PAG-conjugate) will produce a population of molecules with a Poisson distribution of the number of monomeric units per polymer in the conjugate. Thus, a compound described as having a polymer of N=7 monomeric units refers not only to the actual polymers in that population being described as having N=7 monomeric units, but also to a population of molecules with the peak of the distribution being 7. The distribution of monomeric units in a given population can be determined, e.g., by nuclear magnetic resonance (NMR) or by mass spectrometry (MS).

Throughout this application, conventional terminology is used to designate the isomers as described below and in appropriate text books known to those of ordinary skill in the art. (see, e.g., Principles in Biochemistry, Lehninger (ed.), page 99-100, Worth Publishers, Inc. (1982) New York, N.Y.; Organic Chemistry, Morrison and Boyd, 3rd Edition, Chap. 4, Allyn and Bacon, Inc., Boston, Mass. (1978).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

A carbon atom which contains four different substituents is referred to as a chiral center. A chiral center can occur in two different isomeric forms. These forms are identical in all chemical and physical properties with one exception, the direction in which they can cause the rotation of plane-polarized light. These compounds are referred to as being "optically active," i.e., the compounds can rotate the plane-polarized light in one direction or the other.

The four different substituent groups attached to a carbon can occupy two different arrangements in space. These arrangements are not superimposable mirror images of each other and are referred to as optical isomers, enantiomers, or stereoisomers. A solution of one stereoisomer of a given compound will rotate plane polarized light to the left and is called the levorotatory isomer [designated (−)]; the other stereoisomer for the compound will rotate plane polarized light to the same extent but to the right and is called dextrorotatory isomer [designated (+)].

The R S system was invented to avoid ambiguities when a compound contains two or more chiral centers. In general, the system is designed to rank the four different substituent atoms around an asymmetric carbon atom in order of decreasing atomic number or in order of decreasing valance density when the smallest or lowest-rank group is pointing directly away from the viewer. The different rankings are well known in the art and are described on page 99 of *Lehninger*. If the decreasing rank order is seen to be clock-wise, the configuration around the chiral center is referred to as R; if the decreasing rank order is counter-clockwise, the configuration is referred to as S. Each chiral center is named accordingly using this system.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The compositions and pharmaceutical compositions of the present invention comprise one or more of the compounds of the present invention, either in a pure form or a partially pure form. Similarly, the methods of the present invention comprise using one or more compounds, wherein the compounds are in a pure form, a partially pure form.

In one embodiment, a composition of the invention comprises at least one of the compounds of the present invention, i.e. one or more of the compounds represented by the structures of formula I, II, III, IV, VII, A, B, C, D, E, or F. In another embodiment, a composition of the invention comprises a mixture of at least two of the compounds represented by the structures of formula I, II, III, IV, VII, A, B, C, D, E, or F. In another embodiment, a composition of the invention comprises a mixture of at least five of the compounds represented by the structures of formula I, II, III, IV, VII, A, B, C, D, E, or F. In another embodiment, a composition of the invention comprises a mixture of at least ten of the compounds represented by the structures of formula I, II, III, IV, VII, A, B, C, D, E, or F.

It has now been surprisingly found that one or more compounds represented by the structures of formula I, II, III, IV, VII, A, B, C, D, E, or F are effective against a very wide variety of immuno-allergical diseases and conditions. Immuno-allergical diseases are allergy-associated diseases of the immune system. Nonlimiting examples of immuno-allergical diseases against which the compounds of the present invention are active are bronchial asthma, allergic rhinitis, psoriasis and Crohn's disease.

Thus, in one embodiment, the present invention provides a method for the treatment, prevention and control of immuno-allergical diseases in human as well as veterinary applications. In one embodiment, the method comprises administering to a subject one or more compounds represented by the structures of formula I, II, III, IV, VII, A, B, C, D, E, or F. In another embodiment, the method comprises administering to a subject a pharmaceutical composition comprising one or more compounds represented by the structures of formula I, II, III, IV, VII, A, B, C, D, E, or F.

It has now further been surprisingly found that one or more compounds represented by the structures of formula I, II, III, IV, VII, A, B, C, D, E, or F are effective against a very wide variety of autoimmune diseases and conditions. Autoimmune diseases are illnesses that occur when the body tissues are mistakenly attacked by its own immune system. The immune system is a complex organization of cells and antibodies designed normally to "seek and destroy" invaders of the body, particularly infections. Patients with these diseases have antibodies in their blood that target their own body tissues, where they can be associated with inflammation. Nonlimiting examples of autoimmune diseases against which the compounds of the present invention are active are systemic lupus erythematosus, autoimmune thyroiditis, rheumatoid arthritis, diabetes, multiple sclerosis and experimental autoimmune encephalomyelitis.

Thus, in one embodiment, the present invention provides a method for the treatment, prevention and control of autoimmune diseases in human as well as veterinary applications. In one embodiment, the method comprises administering to a subject one or more compounds represented by the structures of formula I, II, III, IV, VII, A, B, C, D, E, or F. In another embodiment, the method comprises administering to a subject a pharmaceutical composition comprising one or more compounds represented by the structures of formula I, II, III, IV, VII, A, B, C, D, E, or F.

It has now further been surprisingly found that one or more compounds represented by the structures of formula I, II, III, IV, VII, A, B, C, D, E, or F are effective against organ or tissue transplantation rejection. In one embodiment, the organ or tissue transplantation rejection is bone-marrow rejection, skin graft rejection, cardiac graft rejection or chronic-graft-versus-host disease.

Thus in one embodiment, the present invention provides a method for the treatment, prevention and control of organ or tissue transplantation rejection in human as well as veterinary applications. In one embodiment, the method comprises administering to a subject one or more compounds represented by the structures of formula I, II, III, IV, VII, A, B, C, D, E, or F. In another embodiment, the method comprises administering to a subject a pharmaceutical composition comprising one or more compounds represented by the structures of formula I, II, III, IV, VII, A, B, C, D, E, or F.

Methods of administration are well known to a person skilled in the art. Methods of administration include but are not limited to parenterally, transdermally, intramuscularly, intravenously, intradermally, intranasally, subcutaneously, intraperitonealy, or intraventricularly or rectally. Methods and means of administration are known to those skilled in the art. For example, U.S. Pat. Nos. 5,693,622; 5,589,466; 5,580,859; and 5,566,064, which are hereby incorporated by reference in their entirety.

In addition, the present invention provides a pharmaceutical composition comprising as an active ingredient one or more compounds of the present invention, together with one or more pharmaceutically acceptable excipients. As used herein, "pharmaceutical composition" can mean a therapeutically effective amount of one or more compounds of the present invention together with suitable excipients and/or carriers useful for the treatment of immuno-allergical diseases, autoimmune diseases, and organ or tissue transplantation rejection. A "therapeutically effective amount" as used herein refers to that amount that provides a therapeutic effect for a given condition and administration regimen. Such compositions can be administered by any one of the methods listed hereinabove.

A further aspect of the invention comprises a compound of the invention in combination with other compounds of the invention. A compound of the invention may also be administered in combination with an anti-inflammatory agent, an immunosuppressant, an antiviral agent, or the like. Furthermore, the compounds of the invention may be administered in combination with a chemotherapeutic agent such as an alkylating agent, anti-metabolite, mitotic inhibitor or cytotoxic antibiotic, as described above. In general, the currently available dosage forms of the known therapeutic agents for use in such combinations will be suitable.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or In multiple, single capsules for each of the therapeutic agents.

Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compositions and combination therapies of the invention may be administered in combination with a variety of pharmaceutical excipients, including stabilizing agents, carriers and/or encapsulation formulations as described herein.

In one embodiment, the compositions of the present invention are formulated as oral or parenteral dosage forms, such as uncoated tablets, coated tablets, pills, capsules, powders, granulates, dispersions or suspensions. In another embodiment, the compositions of the present invention are formulated for intravenous administration. In another embodiment, the compounds of the present invention are formulated in ointment, cream or gel form for transdermal administration. In another embodiment, the compounds of the present invention are formulated as an aerosol or spray for nasal application. In another embodiment, the compositions of the present invention are formulated in a liquid dosage form. Examples of suitable liquid dosage forms include solutions or suspensions in water, pharmaceutically acceptable fats and oils, alcohols or other organic solvents, including esters, emulsions, syrups or elixirs, solutions and/or suspensions.

Suitable excipients and carriers can be solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents Parenteral and intravenous forms should also include minerals and other materials to make them compatible with the type of injection or delivery system chosen.

This invention is further illustrated in the Examples section, which follows. This section is set forth to aid in an understanding of the invention but is not intended to, and should not be construed to, limit in any way the invention as set forth in the claims that follow thereafter.

EXAMPLES

Example 1

Synthesis of Compounds

Compounds of the invention were synthesized and characterized as described below.

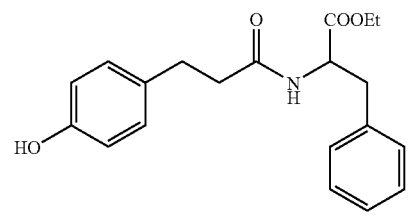

AV 23

$C_{20}H_{23}NO_4$
Mol. Wt.: 341.40

0.66 gr, 4 mM, 4-hydroxy hydrocinnamic acid and 4 ml thionyl chloride in 30 ml cyclohexane were refluxed for 2 hours. Evaporation gave a yellow solid to which were added 0.9 gr, 4 mM, phenyl alanine ethyl ester HCl, 30 ml dichloromethane and 1 ml triethyl amine. After stirring 2 hours at room temperature, water and KOH were added to neutral pH and the reaction extracted with dichloromethane Evaporation gave a light yellow viscous oil, which was triturated and recrystallyzed with ethanol to give 0.25 gr, 18%, white solid, mp-213.

NMR CDCl₃ 7.30-6.9 (9H, m), 4.20 (2H, q, J=7.0 Hz), 3.30 (1H, m) 3.10 (2H, t, J=7.2 Hz) 2.90 (2H, m), 2.60 (2H, t, J=7.2 Hz), 1.35 (3H, t, J=7.0 Hz). MS-341 M⁺, 10%), 277(15), 194(20), 165(M-phenethyl ester, 100%), 149(65) m/e.

AV 24

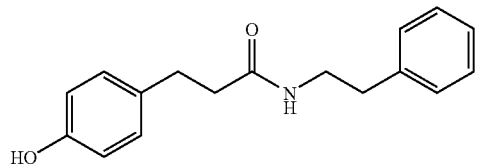

C₁₇H₁₉NO₂
Mol. Wt.: 269.34

0.66 gr, 4 mM, 4-hydroxy hydrocinnamic acid and 4 ml thionyl chloride in 30 ml cyclohexane were refluxed for 2 hours. Evaporation gave light yellow solid to which were added 0.5 gr, 4.1 mM, phenethyl amine, 30 ml dichloromethane and 0.6 ml triethyl amine. After stirring for 2 hours at room temperature, water and KOH were added to neutral pH and the reaction was extracted with dichloromethane. Evaporation gave a viscous oil which was recrystallyzed with ethanol to give 0.3 gr white solid, 28%, mp-165.

NMR acetone d₆ 7.35-6.75 (9H, m), 3.40 (2H, q, J=7.1 Hz), 2.90 (2H, t, J=7.2 Hz) 2.75 (2H, t, J=7.2 Hz), 2.42 (2H, t, J=7.1 Hz). Phenethyl amine-NMR acetone d₆ 7.2 (5H, m), 2.96 (2H, t, J=7.2 Hz) 2.75 (2H, t, J=7.2 Hz). MS-269(M⁺, 100%), 178(M-benzyl) m/e.

AV 26

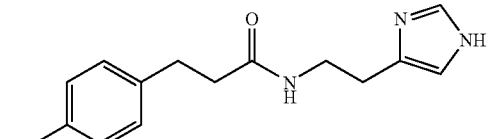

C₁₄H₁₇N₃O₂
Mol. Wt.: 259.30

0.66 gr, 4 mM, 4-hydroxy hydrocinnamic acid and 4 ml thionyl chloride in 30 ml cyclohexane were refluxed for 1.5 hours. Evaporation gave a light yellow solid to which were added 0.5 gr, 4.1 mM, histidine amine, 30 ml dichloromethane and 0.5 ml triethyl amine. After stirring 2 hours at room temperature, water and KOH were added to neutral pH and the reaction was extracted with dichloromethane. Evaporation gave a viscous oil which was recrystallyzed with ethanol to give 0.15 gr white solid, 15%, mp-245.

NMR acetone d₆ 7.35-(6H, m), 3.42 (2H, q, J=7.1 Hz), 2.93 (2H, t, J=7.2 Hz), 2.73 (2H, t, J=7.2 Hz), 2.45 (2H, t, J=7.1 Hz). MS-259(M⁺, 17%), 239(25), 213(18), 194(100%), 185 (37) m/e

AV 27

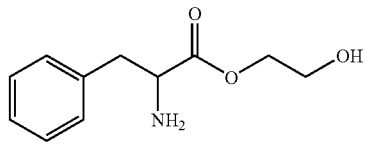

C₁₁H₁₅NO₃
Mol. Wt.: 209.24

3.2 gr DL phenyl alanine, 20 ml ethylene glycol and 7 ml thionyl chloride were refluxed for 2 hours. Workup as above gave 1.3 gr oil which was used in the synthesis of AV 28.

NMR acetone d₆ 7.35-(5H, m), 4.50, 3.27, 2.90 (3H, 12 line ABX), 4.32 (2H, t, J=7.0 Hz), 3.76 (2H, t, J=7.0 Hz).

AV 28

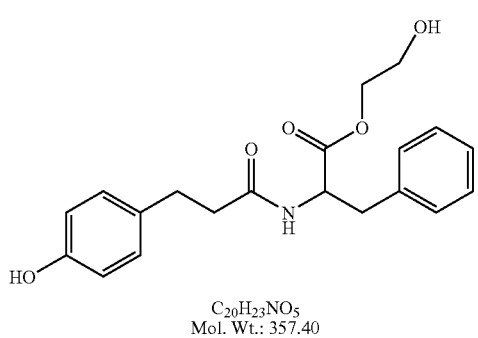

C₂₀H₂₃NO₅
Mol. Wt.: 357.40

1 gr, 6 mM, 4-hydroxy hydrocinnamic acid and 5 ml thionyl chloride in 30 ml cyclohexane were refluxed for 1.5 hours. Evaporation gave a light yellow solid to which were added 1.2 gr AV 27 in 30 ml dichloromethane and 1 ml triethyl amine. After stirring 2 hours at room temperature, water and KOH were added to neutral pH and the reaction was extracted with dichloromethane. Evaporation gave a viscous oil which was recrystallyzed with ethanol to give 0.18 gr white solid, 8%, mp-224.

NMR acetone d₆ 7.35-6.8 (9H, m), 3.73-2.50 (12H, m).

AV 29

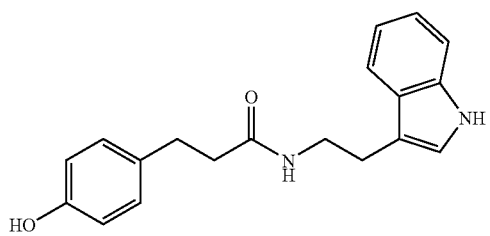

C₁₉H₂₀N₂O₂
Mol. Wt.: 308.37

0.22 gr, 1.3 mM, 4-hydroxy hydrocinnamic acid and 2 ml thionyl chloride in 30 ml cyclohexane were refluxed for 1.5 hours. Evaporation gave a light yellow solid to which were added 0.2 gr, 1.4 mM, tryptamine in 30 ml dichloromethane and 0.3 ml triethyl amine. After stirring 1.5 hours at room temperature, water and KOH were added to neutral pH and the reaction was extracted with dichloromethane. Evaporation gave a viscous oil which was recrystallyzed with ethanol to give 0.11 gr white solid, 27%, mp-136.

NMR acetone d$_6$ 7.36 (2H, d, J=7.8 Hz), 7.0 (8H, m), 3.48 (2H, q, J=7.1 Hz), 3.05 (2H, t, J=7.1 Hz), 2.88 (2H, t, J=7.1 Hz), 2.52 (2H, t, J=7.1 Hz).

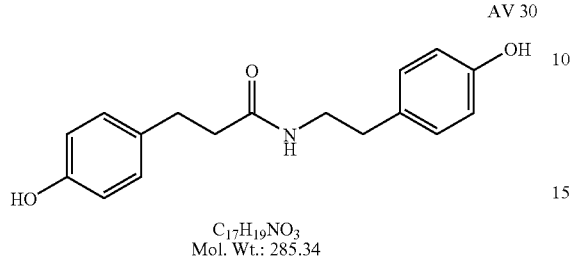

AV 30

C$_{17}$H$_{19}$NO$_3$
Mol. Wt.: 285.34

0.22 gr, 1.3 mM, 4-hydroxy hydrocinnamic acid and 2 ml thionyl chloride in 30 ml cyclohexane were refluxed for 1.5 hours. Evaporation gave light yellow solid to which were added 0.2 gr, 1.5 mM, tyramine, 30 ml dichloromethane and 0.3 ml triethyl amine. After stirring for 2 hours at room temperature, water and KOH were added to neutral pH and the reaction was extracted with dichloromethane. Evaporation gave a viscous oil which was recrystallyzed with ethanol to give 85 mg white solid, 23%.

NMR acetone d$_6$ 7.36 (4H, ABq, J=8.8 Hz), 7.20 (4H, Abq, J=8.6 Hz), 3.48 (2H, q, J=7.1 Hz), 3.05 (2H, t, J=7.1 Hz), 2.88 (2H, t, J=7.1 Hz), 2.52 (2H, t, J=7.1 Hz).

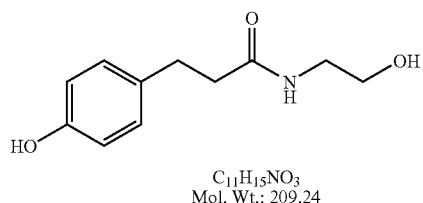

AV 32

C$_{11}$H$_{15}$NO$_3$
Mol. Wt.: 209.24

A. 0.8 gr 4-hydroxy cinnamic acid in 40 ml methanol and 10 drops HCl were refluxed for 12 hours. Workup as above gave 0.6 gr oil, 68% yield.

NMR CDCl$_3$ 7.02, 6.75 (4H, Abq, J=8.6 Hz), 3.66 (3H, s), 2.86 (2H, t, J=7.4 Hz), 2.60 (2H, t, J=7.4 Hz).

B. 0.6 gr, 3.3 mM, ester from step A and 0.26 gr, 4.2 mM, ethanol amine were heated at 100 for 3 hours in an open vessel. Chromatography gave 0.3 gr recovered ester followed by amide. The viscous oil was triturated with acetone-methylene chloride and filtered to give 160 mg white solid, 23% yield, mp-102.

NMR acetone d$_6$ 8.10 (1H, s, OH), 7.03, 6.74 (4H, Abq, J=8.8 Hz), 3.90 (1H, t, J=5.2 Hz, NH), 3.54 (2H, q, J=7.1 Hz), 3.28 (2H, t, J=7.1 Hz), 2.80 (2H, t, J=8.2 Hz), 2.41 (2H, t, J=8.2 Hz).

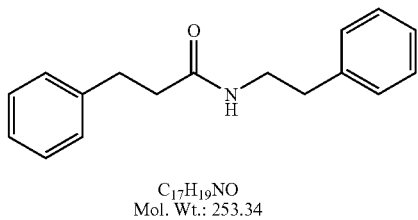

AV 33

C$_{17}$H$_{19}$NO
Mol. Wt.: 253.34

0.9 gr, 6 mM, hydrocinnamic acid and 0.6 gr, 6 equivalents, triphosgen in 30 ml dichloromethane and 1.5 ml triethyl amine were stirred 10 minutes at room temperature and 0.7 gr phenethyl amine were added. After 2 hours at room temperature, workup (HCl) gave a viscous oil which was recrystalyzed with hexane-methylene chloride to give 166 mg white solid, 11%, mp-91.

NMR acetone d$_6$ 7.35 (10H, m), 3.40 (2H, q, J=7.2 Hz), 2.90 (2H, t, J=7.4 Hz), 2.74 (2H, t, J=7.2 Hz), 2.46 (2H, t, J=7.4 Hz).

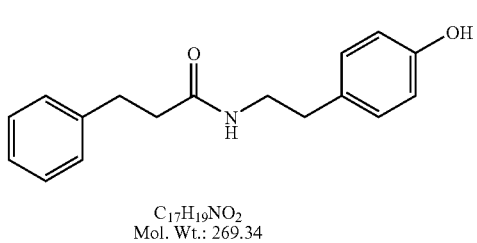

AV 34

C$_{17}$H$_{19}$NO$_2$
Mol. Wt.: 269.34

Prepared as AV 33, in the same amount but with tyramine instead of phenethyl amine. Chromatography and trituration with benzene-hexane gave 220 mg white solid, 14%, mp-98.

NMR acetone d$_6$ 7.25 (5H, m), 6.96, 6.75 (4H, Abq, J=8.4 Hz), 3.43 (2H, q, J=6.8 Hz), 2.94 (2H, t, J=7.6 Hz), 2.65 (2H, t, J=6.8 Hz), 2.42 (2H, t, J=7.6 Hz).

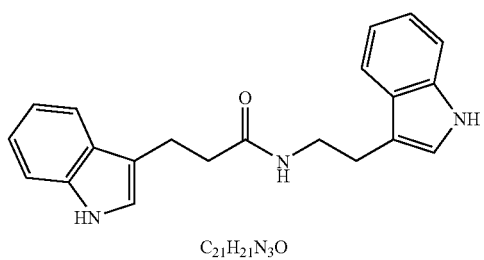

AV 35

C$_{21}$H$_{21}$N$_3$O
Mol. Wt.: 331.41

Prepared as AV 33, 3 mM, from indole propionic acid and tryptamine. Chromatography and trituration with ethanol gave 162 mg white solid, 16%, mp-142.

NMR acetone d$_6$ 7.57 (2H, d, J=7.8 Hz), 7.36 (2H, d, J=7.8 Hz), 7.0 (8H, m), 3.48 (2H, q, J=7.1 Hz), 3.05 (2H, t, J=7.1 Hz), 2.88 (2H, t, J=7.1 Hz), 2.52 (2H, t, J=7.1 Hz).

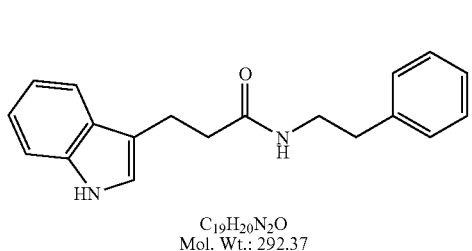

AV 38

C$_{19}$H$_{20}$N$_2$O
Mol. Wt.: 292.37

Prepared as AV 33, 2 mM, from indole propionic acid and phenethyl amine. Chromatography and trituration with ethanol gave 220 mg white viscous oily solid, 37%.

NMR acetone d$_6$ 7.57 (2H, d, J=7.8 Hz)), 7.25-6.97 (9H, m), 3.44 (2H, q, J=7.1 Hz), 3.10 (2H, t, J=7.1 Hz), 2.66(2H, t, J=7.1 Hz), 2.51 (2H, t, J=7.1 Hz).

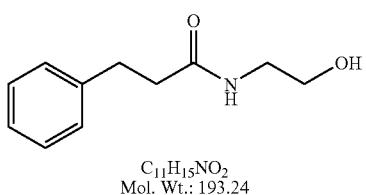

AV 43

C$_{11}$H$_{15}$NO$_2$
Mol. Wt.: 193.24

0.9 gr, 6 mM, hydrocinnamic acid and 0.6 gr, 6 equivalents, triphosgen in 30 ml dichloromethane and 1 ml triethyl amine were stirred for 10 minutes at room temperature and 0.6 gr ethanol amine were added. After 2 hours at room temperature, workup (HCl) gave a viscous oil which was recrystalyzed with hexane to give 124 mg white solid, 11%, mp-91.

NMR acetone d$_6$ 7.30 (5H, m), 3.63 (2H, t, J=5.2 Hz), 3.36 (2H, q, J=5.2 Hz), 2.97 (2H, t, J=7.3 Hz), 2.50 (2H, t, J=7.3 Hz).

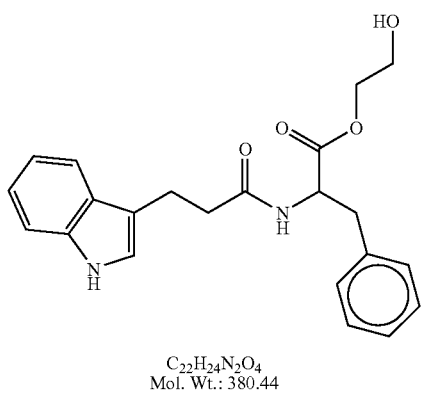

AV 45

C$_{22}$H$_{24}$N$_2$O$_4$
Mol. Wt.: 380.44

Prepared similar to AV 28, but with the triphosgen method, from 6 mM indole propionic acid, AV 27. Chromatography gave 0.35 gr viscous oil, 13% yield.

NMR CDCl$_3$ 7.95 (1H(br.s), 7.57 (2H, d, J=8.0 Hz), 7.36-6.90 (9H, m), 4.36 (2H, t, J=7.1 Hz), 4.17 (2H, q, J=7.0 Hz), 3.5-2.8 (7H, m).

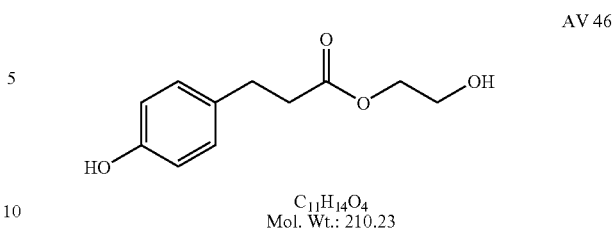

AV 46

C$_{11}$H$_{14}$O$_4$
Mol. Wt.: 210.23

0.65 gr, 3.9 mM, 4-hydroxy hydro cinnamic acid, 15 ml ethylene glycol and 5 ml thionyl chloride were refluxed 3 hours. Workup gave 0.5 gr 61%, oil.

NMR acetone d$_6$ 7.02, 6.76 (4H, ABq, J=8.6 Hz), 4.28 (2H, t, J=7.1 Hz), 3.63 (2H, t, J=7.1 Hz), 2.85, 2.63 (4H, m).

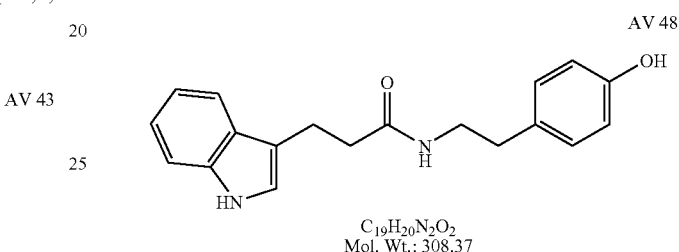

AV 48

C$_{19}$H$_{20}$N$_2$O$_2$
Mol. Wt.: 308.37

Prepared as AV 33, 3 mM, from indole propionic acid and tyramine. Chromatography and trituration with ethanol-hexane gave 120 mg pink-white solid, 13%.

NMR acetone d$_6$ 7.57 (2H, d, J=7.8 Hz)), 7.25-6.97 (8H, m), 3.44 (2H, q, J=7.1 Hz), 3.10 (2H, t, J=7.1 Hz), 2.66 (2H, t, J=7.1 Hz), 2.51 (2H, t, J=7.1 Hz).

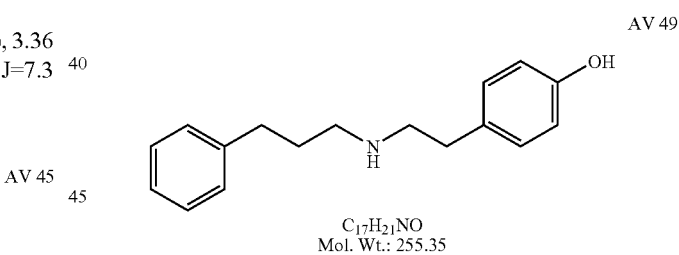

AV 49

C$_{17}$H$_{21}$NO
Mol. Wt.: 255.35

To 0.7 gr, 5 mM, hydro cinnamic aldehyde and 0.7 gr, 5 mM, tyramine in 20 ml ethanol was added 0.4 gr NaBH$_4$ and the reaction refluxed 1 hour. Workup gave 0.7 gr viscous oil, 55% yield.

NMR acetone d$_6$ 7.35 (5H, m), 7.15, 6.85 (4H, ABq, J=8.6 Hz), 2.85 (2H, t, J=6.7 Hz), 2.70 (6H, m), 1.80 (2H, quin., J=7.2 Hz).

Example 2

Synthesis of Polyalkylene Glycol Compounds

Polyalkylene glycol compounds were generally synthesized by preparation of the appropriate alcohol compound (e.g., one of the compounds described in Example 1, or a hydroxylated derivative thereof) and then conjugation of the alcohol with a polyalkylene glycol (PAG) polymer (e.g., polyethylene glycol (PEG) or polypropylene glycol (PPG)) of the desired length.

Compound 1, Phenyl Alaninol 1.2 gr, 32 mM, of LiAlH₄ were added to 2.3 gr, 10 mM, phenyl alanine ethyl ester HCl in 50 ml dry ether. After stirring for 2 hours at room temperature, water and KOH were added and the reaction product was extracted with ethyl acetate. After evaporation, 0.8 gr of compound 1, a light yellow oil, was obtained.

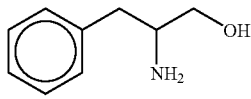

C$_9$H$_{13}$NO
Mol. Wt.: 151.21

Compound 1 crystallized on standing. Mp-70.

NMR CDCl$_3$ 7.30 (5H, m), 3.64 (1H, dd, J=10.5, 3.8 Hz) 3.40 (1H, dd, J=10.5, 7.2 Hz) 3.12 (1H, m), 2.81 (1H, dd, J=13.2, 5.2 Hz), 2.52 (1H, dd, J=13.2, 8.6 Hz) NMR acetone d$_6$ 7.30 (5H, m), 3.76 (1H, dt) 3.60 (1H, m) 3.30 (1H, t), 2.85 (2H, m). Helv. Chim. Acta, 31, 1617(1948). Biels.-E3, Vol. 13, p 1757.

Compound 2, Tyrosinol

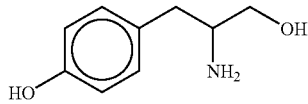

C$_9$H$_{13}$NO$_2$
Mol. Wt.: 167.21

To 3 gr, 12 mM, L-tyrosine ethyl ester HCl in 50 ml dry ether was added 1.2 gr 32 mM LiAlH$_4$. After stirring 3 hours at room temperature, water and KOH were added and the reaction was extracted with ethyl acetate. Evaporation gave 1.1 gr of a light yellow oil, 54% yield, which on standing crystallized. mp-85.

NMR CDCl$_3$ 7.20 (4H, AB q, J=8.6 Hz), 3.50 (2H, m) 3.20 (1H, m), 2.81 (2H, m). NMR tyrosine ethyl ester free base CDCl$_3$ 7.0, 6.56 (4H, AB q, J=8.8 Hz), 4.20 (2H, q, J=7,0 Hz), 3.70, 3.0, 2.80 (3H, 12 line ABXm), 1.28. (3H, t, J=7.0 Hz). JACS, 71, 305(1949). Biels.-E3, Vol. 13, p 2263.

Compound 3, Tyrptophanol

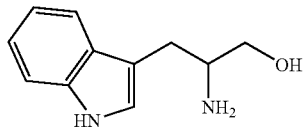

C$_{11}$H$_{14}$N$_2$O
Mol. Wt.: 190.24

To 3 gr, 12.9 mM, L-tryptophan methyl ester HCl in 50 ml dry ether was added 1.2 gr, 32 mM LiAlH$_4$. After stirring 6 hours at room temperature water and KOH were added and the reaction extracted with ethyl acetate. Evaporation gave 1.23 gr light yellow oil, 50% yield. On standing crystallized. Mp-65.

NMR CDCl$_3$ 7.30 (5H, m), 3.64 (1H, dd, J=10.5, 3.8 Hz) 3.40 (1H, dd, J=10.5, 7.2 Hz) 3.12 (1H, m), 2.81 (1H, dd, J=13.2, 5.2 Hz), 2.52 (1H, dd, J=13.2, 8.6 Hz) J. Het. Chem, 13, 777(1976). Biels.-E5, 22, Vol. 12, p 90.

Compound 4, AV 22

0.66 gr 4-hydroxy hydrocinnamic acid and 4 ml thionyl chloride in 30 ml cyclohexane were refluxed for 2 hours. After evaporation, a white solid was obtained, to which 0.65 gr oil of Compound 1 (4.3 mM) in 30 ml dichloromethane and 0.4 ml triethyl amine were added. After stirring for 2 hours at room temperature, water and KOH were added in order to neutralize the pH. The reaction product was extracted with dichloromethane. Evaporation gave 0.8 gr of compound 4, light yellow viscous oil. Part of this product was triturated and recrystallized with ethanol to give a white solid. Mp-149.

NMR CDCl$_3$ 7.30-6.9 (9H, m), 3.50 (2H, m) 3.30 (2H, t, J=7.2 Hz) 2.90 (3H, m), 2.60 (2H, t, J=7.2 Hz).

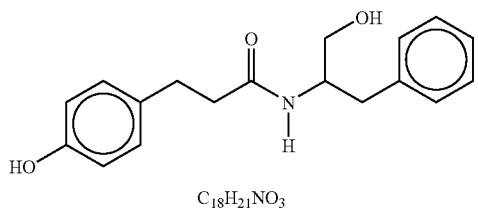

C$_{18}$H$_{21}$NO$_3$
Mol. Wt.: 299.36

Compound 5, AV 57

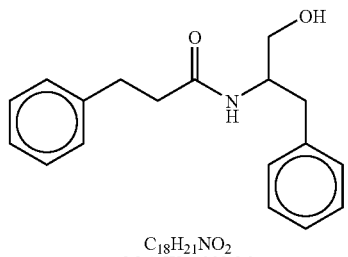

C$_{18}$H$_{21}$NO$_2$
Mol. Wt.: 283.36

0.75 gr, 5 mM, hydrocinnamic acid and 4 ml thionyl chloride in 30 ml cyclohexane were refluxed for 2 hours. Evaporation gave a white solid to which were added 0.83 gr, 5.5 mM, phenyl alaninol in 30 ml dichloromethane and 0.5 ml triethyl amine. After stirring 3 hours at room temperature, water and KOH were added to neutral pH and the reaction was extracted with dichloromethane. Evaporation gave 0.57 gr of a yellow viscous oil, 40% yield.

NMR CDCl$_3$ 7.40-7.10 (10H, m), 3.60 (2H, m) 3.35 (2H, t, J=7.2 Hz) 2.95 (3H, m), 2.50 (2H, t, J=7.2 Hz).

Compound 6, AV 58

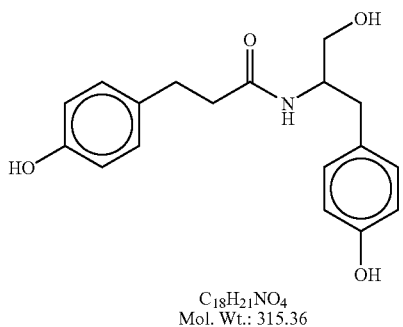

C<sub>18</sub>H<sub>21</sub>NO<sub>4</sub>
Mol. Wt.: 315.36

0.66 gr, 4 mM, 4-hydroxy hydrocinnamic acid and 4 ml thionyl chloride in 30 ml cyclohexane were refluxed 3 hours. Evaporation gave a light yellow solid to which were added 0.72 gr, 4.3 mM, tyrosinol in 30 ml dichloromethane and 0.5 ml triethyl amine. After stirring 3 hours at room temperature, water and KOH were added to neutral pH and the reaction was extracted with dichloromethane. Evaporation gave 0.53 gr light yellow viscous oil, 42% yield.

NMR CDCl$_3$ 7.30, 7.20 (8H, 2 ABq, J=8.6 Hz), 3.40 (2H, m) 3.30 (2H, t, J=7.2 Hz) 2.90 (3H, m), 2.60 (2H, t, J=7.2 Hz).

Compound 7 AV 59

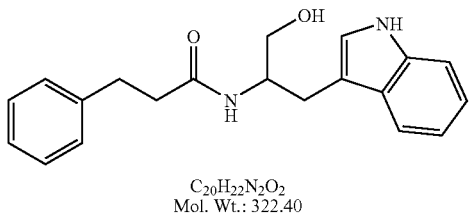

C$_{20}$H$_{22}$N$_2$O$_2$
Mol. Wt.: 322.40

0.45 gr, 3 mM, hydrocinnamic acid and 3 ml thionyl chloride in 30 ml cyclohexane were refluxed for 2 hours. Evaporation gave a light yellow solid to which were added 0.66 gr, 3.5 mM, tryptophanol in 30 ml dichloromethane and 0.4 ml triethyl amine. After stirring 3 hours at room temperature, water and KOH were added to neutral pH and the reaction was extracted with dichloromethane. Evaporation gave 0.61 gr viscous oil, 63% yield.

NMR CDCl$_3$ 7.50-7.05 (10H, m), 3.65 (2H, m) 3.32 (2H, t, J=7.3 Hz) 2.92 (3H, m), 2.53 (2H, t, J=7.3 Hz).

Compound 8, AV 72

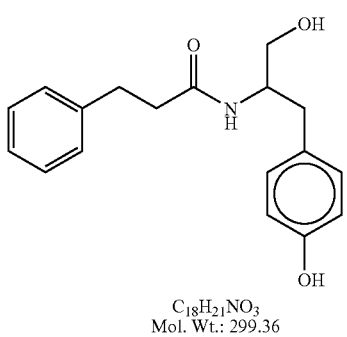

C$_{18}$H$_{21}$NO$_3$
Mol. Wt.: 299.36

0.45 gr, 3 mM, hydrocinnamic acid and 3 ml thionyl chloride in 30 ml cyclohexane were refluxed for 2 hours. Evaporation gave a light yellow solid to which were added 0.58 gr, 3.5 mM, tyrosinol in 30 ml dichloromethane and 0.4 ml triethyl amine. After stirring for 2.5 hours at room temperature, water and KOH were added to attain neutral pH and the reaction was extracted with dichloromethane. Evaporation gave 0.57 gr light yellow viscous oil, 63% yield.

NMR CDCl$_3$ 7.40-7.10 (9H, m),3.60 (2H, m) 3.35 (2H, t, J=7.2 Hz) 2.95 (3H, m), 2.50 (2H, t, J=7.2 Hz).

Compound 9, AV 73

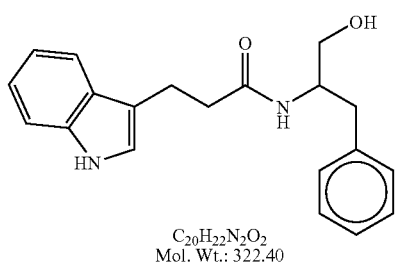

C$_{20}$H$_{22}$N$_2$O$_2$
Mol. Wt.: 322.40

0.38 gr, 2 mM, 3-indole propionic acid and 2 ml thionyl chloride in 30 ml cyclohexane were refluxed for 2 hours. Evaporation gave light yellow solid to which were added 0.4 gr, 2.6 mM, phenyl alaninol in 30 ml dichloromethane and 0.3 ml triethyl amine. After stirring 2.5 hours at room temperature, water and KOH were added to neutral pH and the reaction was extracted with dichloromethane. Evaporation gave 0.47 gr pink solid, 75% yield.

NMR CDCl$_3$ 7.58 (1H, d, J=8.0 Hz), 7.40 (1H, d, J=8.0 Hz), 7.30-6.9 (8H, m), 3.50 (2H, m) 3.30 (2H, t, J=7.5 Hz), 2.95 (3H, m), 2.70 (2H, t, J=7.5 Hz).

Compound 10

0.3 gr of Compound 4 (AV 22), 0.8 gr, triphenyl phosphine and 0.55 gr ethyl diazo carboxylate were added to 1 gr of poly(propylene glycol), (average molecular weight ca 1000), in 60 ml dichloromethane. Stirring for 2 hours at room temperature, evaporation and chromatography gave 0.65 gr of Compound 10, Formula VII, as a viscous oil.

10 (VII)

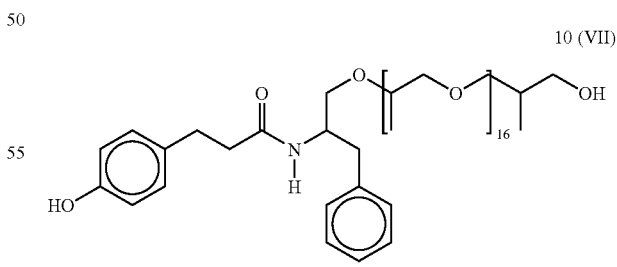

Additional Compounds Synthesized from Phenyl Alaninol

These compounds include those represented by the following formula:

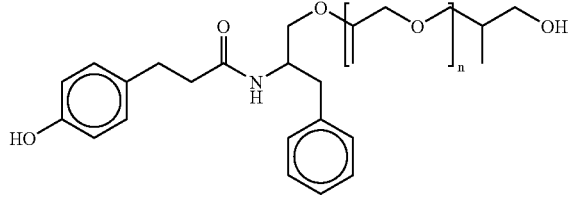

This compound can also be represented as Formula A, where R is a polypropylene glycol polymer and N is the total number of polypropylene monomers in the polymer:

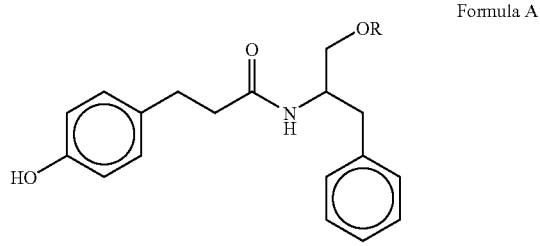

Formula A

AV 61:
R=PPG (polypropylene glycol) N=7 MW-706

0.3 gr AV 22 (1 mM), 0.8 gr, 3 mM, triphenyl phosphine and 0.55 gr 3.2 mM, ethyl diazo carboxylate were added to 1 gr of poly(propylene glycol) (average mol. weight 424, N=7) in 60 ml dichloromethane. After stirring for 4 hours at room temperature, evaporation and chromatography gave 0.55 gr viscous oil, a 73% yield.

NMR CDCl$_3$ 7.30-6.9 (9H, m), 4.1-3.0 (m), 2.60 (2H, t, J=7.2 Hz), 1.2-1.1 (m)

AV 62
R=PPG N=12 MW-996
Was prepared as above from 0.2 gr AV 22 to give 0.3 gr, 46% yield.

AV 60
R=PPG N=17 MW-1286
Was prepared as above from 0.1 gr AV 22 to give 0.2 gr, 48% yield.

AV 63
R=PPG N=34 MW-2274
Was prepared as above from 0.1 gr AV 22 to give 0.25 gr, 34% yield.

Compounds Synthesized from Compound 5, AV 57

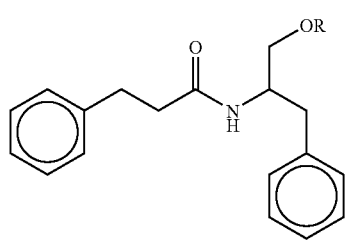

Formula B

AV86
R=PPG N=7 MW-690
Was prepared as above from 0.22 gr AV 57 to give 0.25 gr, 47% yield.

AV 87
R=PPG N=17 MW-1270
Was prepared as above from 0.2 gr AV 57 to give 0.33 gr, 33% yield.

Compounds Synthesized from Compound 9, AV 73

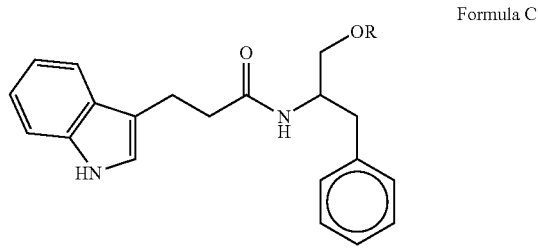

Formula C

AV76
R=PPG N=7 MW-729
Was prepared similar to AV 61 above from 0.22 gr AV 73 to give 0.23 gr, 47% yield.

AV77
R=PPG N=34 MW-2297
Was prepared as above from 0.2 gr AV 73 to give 0.35 gr, 25% yield.

Compounds Synthesized from Tyrosinol

Compounds Synthesized from Compound 6, AV 58

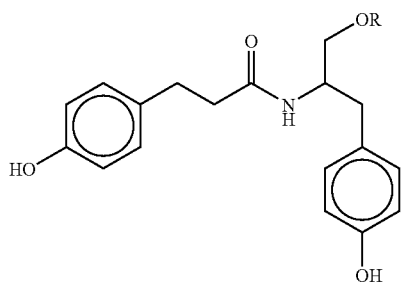

Formula D

AV64
R=PPG N=7 MW-722
Was prepared as above from 0.2 gr AV 58 to give 0.21 gr, 46% yield.

AV65
 R=PPG N=17 MW-1302
 Was prepared as above from 0.23 gr AV 58 to give 0.28 gr, 29% yield.

Compounds Synthesized from Compound 8, AV 72

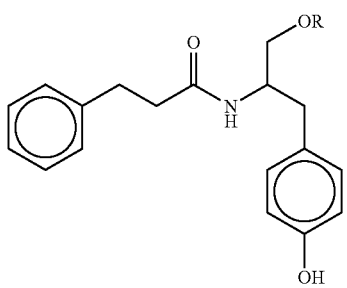

Formula E

AV 74
 R=PPG N=7 MW-706
 Was prepared similar to AV 61, above, from 0.22 gr AV 72 to give 0.26 gr, 50% yield.

AV75
 R=PPG N=34 MW-2274
 Was prepared as above from 0.2 gr AV 72 to give 0.35 gr, 23% yield.

AV 131
 R=PPG N=69 MW-4307
 Was prepared as above from AV 72 and poly(propylene glycol (average mol. weight 4,000).

Compounds Synthesized from Tyrptophanol

Compounds Synthesized from Compound 7, AV 59

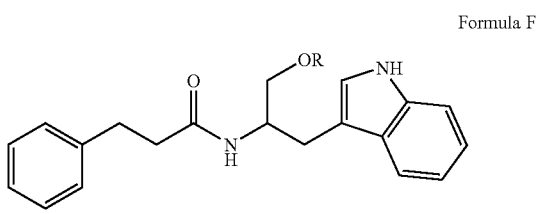

Formula F

AV 81
 R=PPG N=7 MW-729
 Was prepared similar to AV 61, above, from 0.22 gr AV 59 to give 0.26 gr, 53% yield.

AV 82
 R=PPG N=34 MW-2297
 Was prepared as above from 0.2 gr AV 59 to give 0.35 gr, 41% yield.

Example 3

Effect of Compounds on Proliferation Responses of Splenocytes

Spleen cells obtained from native or concanavalin A (Con A)-treated mice were examined in-vitro for their response to T-cell-dependent mitogens. Cells were plated in quadruplicate in 96-well, flat-bottom, microtiter plates ($4 \times 10^5$ cells/0.2 ml/well) in RPMI-1640 medium supplemented with 5% heat inactivated FCS, 2 mM L-glutamine, 100 U/ml penicillin, 100 mg/ml streptomycin and various concentrations of compound 10 (100 µg/ml-100 µg/ml). All plates were incubated for 48 h in humidified atmosphere of 5% $CO_2$ in air at 37° C., and then pulsed for 18 h with 1 mCi $^3$[H] thymidine. Cells from each microculture were harvested on fiberglass filters using a multiharvester, and incorporated radioactivity was measured using standard scintillation techniques.

Incubation with compound 10 has led to a significant inhibition in the proliferation of the splenocytes (Table 1).

TABLE 1

| Concentration of Compound 10 | No Con A | Con A 1 | Con A 2 |
|---|---|---|---|
| 100 µg/ml | 170 | 598 | 1380 |
| 1 µg/ml | 333 | 986 | 2156 |
| 100 ng/ml | 274 | 880 | 2489 |
| 1 ng/ml | 284 | 733 | 3609 |
| 100 pg/ml | 271 | 1280 | 3481 |
| 0 (control) | 837 | 8775 | 42551 |

The effect of AV 75, AV 77, AV 82, AV 86, AV, 87, and a combination of AV 75 and AV 77 on splenocytes was also tested.

Figure 2:
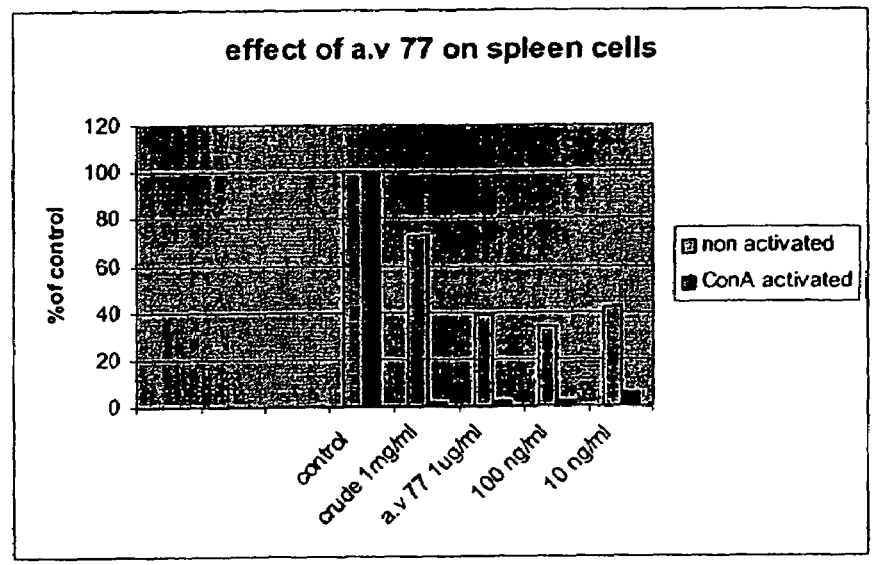
FIG. 2 is a bar graph depicting the effect of AV 77 on spleen cells±ConA.
Figure 3:
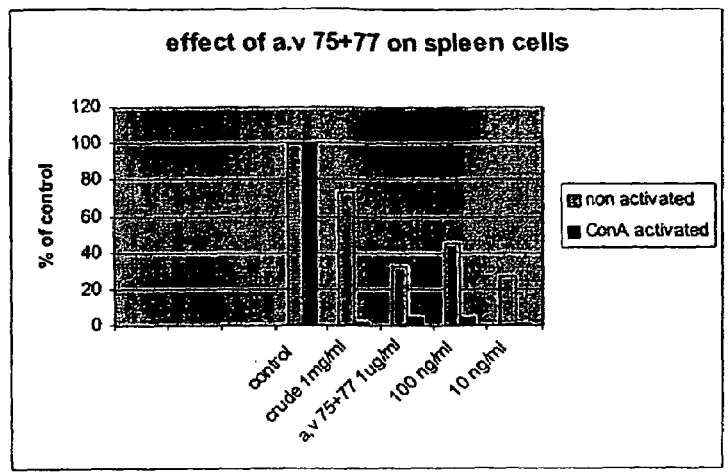
FIG. 3 is a bar graph depicting the effect of AV 75±AV 77 on spleen cells±ConA.
Figure 4:
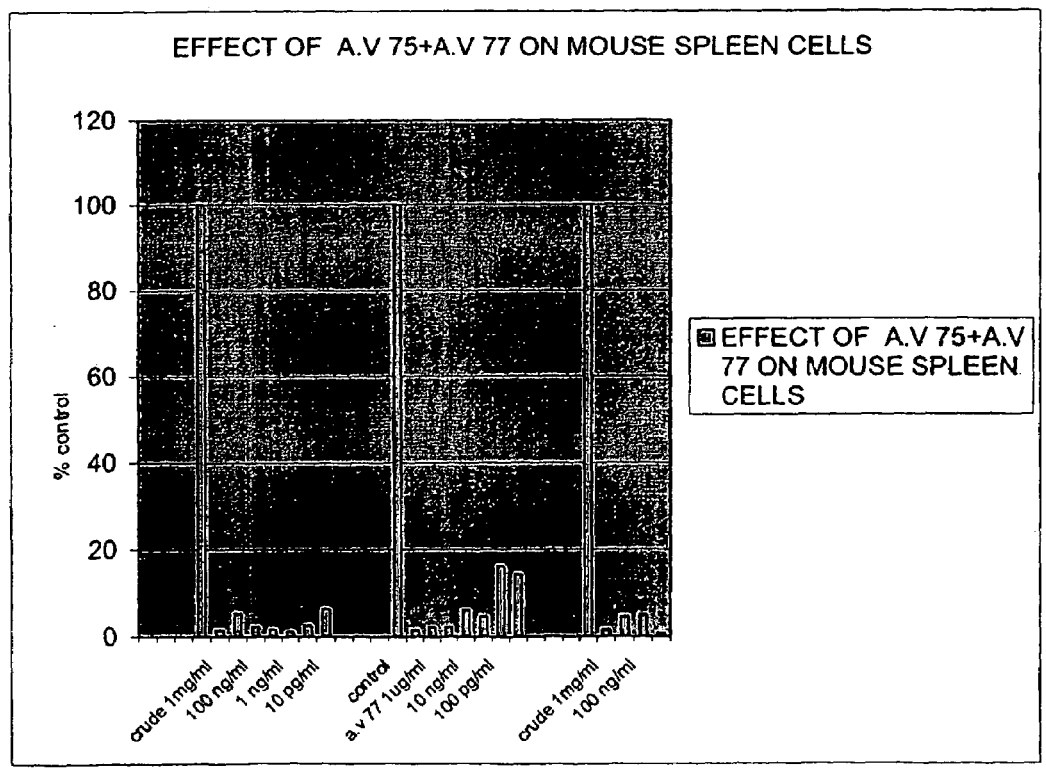
FIG. 4 is a bar graph summarizing the effect of AV 75 and AV 77 on spleen cells±ConA.

Data from the AV 75 experiment is shown in Table 2, and summarized in FIG. 1. Data from the AV 77 experiment is shown in Table 3, and summarized in FIG. 2. Data from the AV 75+AV 77 experiment is shown in Table 4, and summarized in FIG. 3. A comparison of the experiments is shown graphically in FIG. 4. In all figures herein, "crude" refers to crude "Antiviran", an extract from *Bacillus subtilis* var. *indolasus*. See, e.g., PCT publication WO 99/03350.

TABLE 2

| Concentration of AV 75 | Cpm control | Cpm Con A | No Con A (% of control) | Con A (% of control) |
|---|---|---|---|---|
| Control | 553 | 30790 | 100 | 100 |
| Crude 1 mg/ml | 405 | 499 | 73.2 | 1.6 |
| AV 75 1 ug/ml | 339 | 1608 | 61.3 | 5.2 |
| AV 75 100 ng/ml | 324 | 725 | 58.5 | 2.3 |
| AV 75 10 ng/ml | 167 | 529 | 30.2 | 1.7 |
| AV 75 1 ng/ml | 199 | 339 | 35.9 | 1.1 |
| AV 75 100 pg/ml | 184 | 803 | 33.2 | 2.6 |
| AV 75 10 pg/ml | 126 | 1994 | 22.7 | 6.4 |

TABLE 3

| Concentration of AV 77 | Cpm control | Cpm Con A | No Con A (% of control) | Con A (% of control) |
|---|---|---|---|---|
| control | 553 | 30790 | 100 | 100 |
| crude 1 mg/ml | 405 | 499 | 73.2 | 1.6 |
| AV 77 1 ug/ml | 216 | 678 | 39 | 2.2 |
| 100 ng/ml | 190 | 705 | 34.3 | 2.2 |
| 10 ng/ml | 235 | 1903 | 42.5 | 6.1 |
| 1 ng/ml | 189 | 1474 | 34.1 | 4.7 |
| 100 pg/ml | 242 | 5007 | 43.7 | 16.2 |
| 10 pg/ml | 169 | 4427 | 30.5 | 14.3 |

TABLE 4

| Concentration of AV 75 + AV 77 | Cpm control | Cpm Con A | No Con A (% of control) | Con A (% of control) |
|---|---|---|---|---|
| control | 553 | 30790 | 100 | 100 |
| crude 1 mg/ml | 405 | 499 | 73.2 | 1.6 |
| AV 75 + 77 1 ug/ml | 182 | 1439 | 32.9 | 4.6 |
| 100 ng/ml | 250 | 1523 | 45.2 | 4.9 |
| 10 ng/ml | 149 | 240 | 26.9 | 0.7 |
| 1 ng/ml | 206 | 2297 | 37.2 | 7.4 |
| 100 pg/ml | 181 | 942 | 32.7 | 3 |
| 10 pg/ml | 101 | 1420 | 18.2 | 4.6 |

Figure 5:
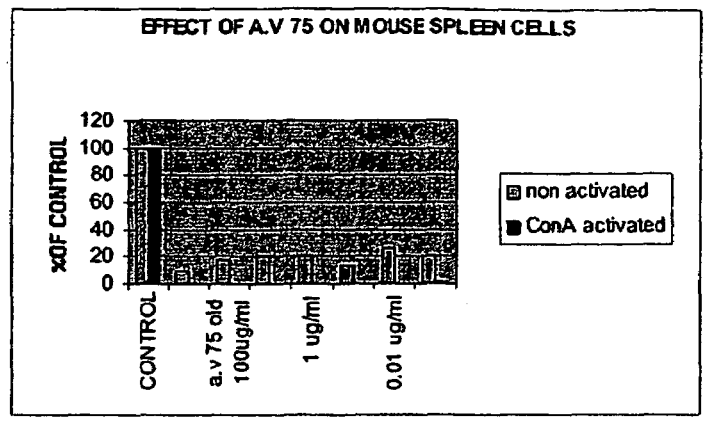
FIG. 5 is a bar graph depicting the effect of AV 75 on spleen cells±ConA.
Figure 6:
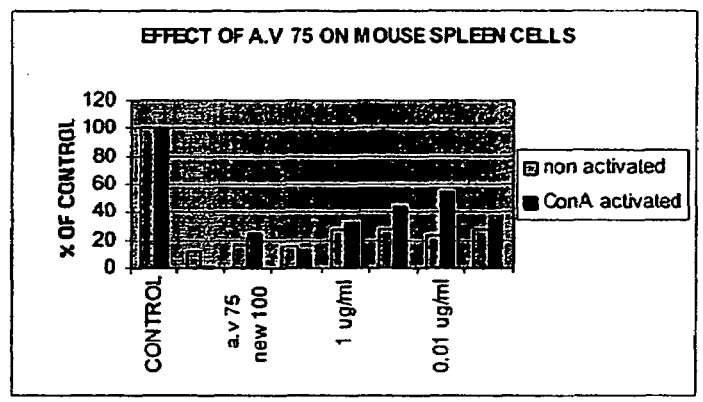
FIG. 6 is a bar graph depicting the effect of AV 75 on spleen cells±ConA.

Additional AV 75 experiments were performed. Data from these AV 75 experiments is shown in Tables 5 and 6, and is summarized in FIGS. 5 and 6.

TABLE 5

| Concentration of AV 75 | Cpm control | Cpm Con A | No Con A (% of control) | Con A (% of control) |
|---|---|---|---|---|
| CONTROL | 1433 | 52111 | 100 | 100 |
| CRUDE 1 mg/ml | 132 | 176 | 9.2 | 0.33 |
| AV 75 old 100 ug/ml | 254 | 189 | 17.7 | 0.36 |
| 10 ug/ml | 302 | 250 | 21 | 0.47 |
| 1 ug/ml | 302 | 348 | 21 | 0.66 |
| 0.1 ug/ml | 198 | 220 | 13.8 | 0.42 |
| 0.01 ug/ml | 370 | 273 | 25.8 | 0.52 |
| 0.001 ug/ml | 285 | 766 | 19.8 | 1.47 |

TABLE 6

| Concentration of AV 75 | Cpm control | Cpm Con A | No Con A (% of control) | Con A (% of control) |
|---|---|---|---|---|
| CONTROL | 1277 | 32124 | 100 | 100 |
| CRUDE 1 mg/ml | 152 | 261 | 11.9 | 0.81 |
| AV 75 new 100 ug/ml | 211 | 8070 | 16.5 | 25.1 |
| 10 ug/ml | 196 | 4054 | 15.3 | 12.6 |
| 1 ug/ml | 350 | 10300 | 27.4 | 32 |
| 0.1 ug/ml | 349 | 14365 | 27.3 | 44.7 |
| 0.01 ug/ml | 293 | 17536 | 22.9 | 54.5 |
| 0.001 ug/ml | 347 | 12088 | 27.1 | 37.6 |

Figure 7:
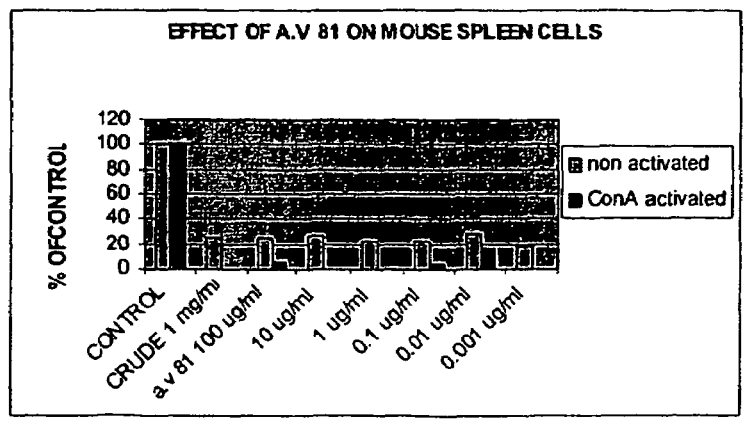
FIG. 7 is a bar graph depicting the effect of AV 81 on spleen cells±ConA.
Figure 8:
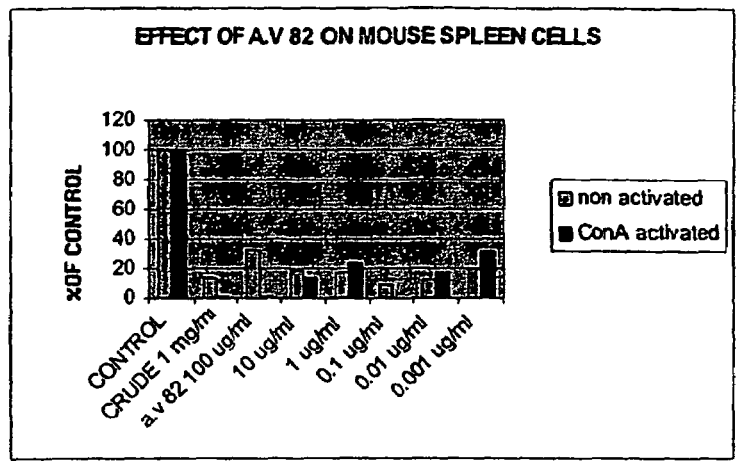
FIG. 8 is a bar graph depicting the effect of AV 82 on spleen cells±ConA.
Figure 9:
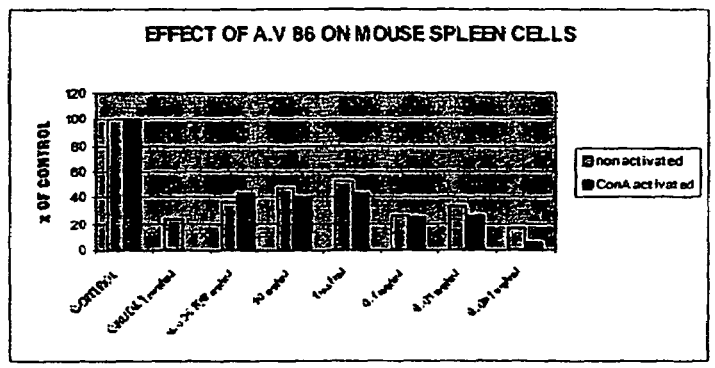
FIG. 9 is a bar graph depicting the effect of AV 86 on spleen cells±ConA.
Figure 10:
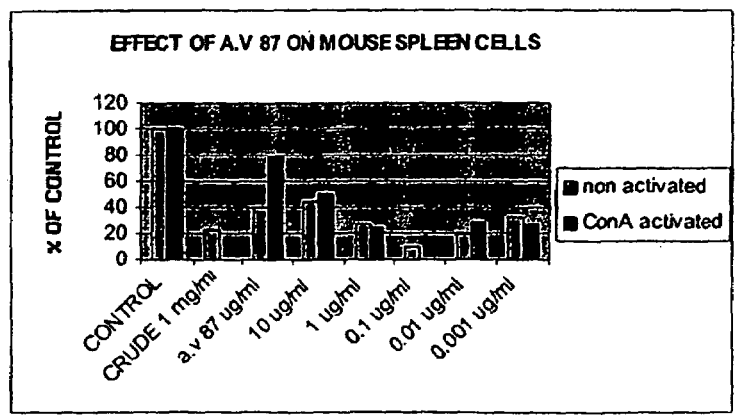
FIG. 10 is a bar graph depicting the effect of AV 87 on spleen cells±ConA.

Data from the AV 81 experiment is shown in Table 7, and summarized in FIG. 7. Data from the AV 82 experiment is shown in Table 8, and summarized in FIG. 8. Data from the AV 86 experiment is shown in Table 9, and summarized in FIG. 9. Data from the AV 87 experiment is shown in Table 10, and summarized in FIG. 10.

TABLE 7

| Concentration of AV 81 | Cpm control | Cpm Con A | No Con A (% of control) | Con A (% of control) |
|---|---|---|---|---|
| CONTROL | 1270 | 54504 | 100 | 100 |
| CRUDE 1 mg/ml | 333 | 212 | 26.2 | 0.38 |
| AV 81 100 ug/ml | 328 | 3109 | 25.8 | 5.7 |
| 10 ug/ml | 350 | 347 | 27.5 | 0.63 |
| 1 ug/ml | 286 | 372 | 22.5 | 0.68 |
| 0.1 ug/ml | 278 | 2440 | 21.8 | 4.47 |
| 0.01 ug/ml | 368 | 8664 | 28.9 | 15.9 |
| 0.001 ug/ml | 224 | 310 | 17.6 | 0.5 |

TABLE 8

| Concentration of AV 82 | Cpm control | Cpm Con A | No Con A (% of control) | Con A (% of control) |
|---|---|---|---|---|
| CONTROL | 1322 | 36600 | 100 | 100 |
| CRUDE 1 mg/ml | 185 | 261 | 13.9 | 0.71 |
| AV 82 100 ug/ml | 435 | 507 | 32.9 | 1.38 |
| 10 ug/ml | 254 | 4831 | 18.5 | 13.2 |
| 1 ug/ml | 232 | 8896 | 17.5 | 24.3 |
| 0.1 ug/ml | 121 | 112 | 9.1 | 0.3 |
| 0.01 ug/ml | 164 | 6494 | 12.4 | 17.7 |
| 0.001 ug/ml | 264 | 11259 | 19.9 | 30.7 |

TABLE 9

| Concentration of AV 86 | Cpm control | Cpm Con A | No Con A (% of control) | Con A (% of control) |
|---|---|---|---|---|
| CONTROL | 1576 | 62506 | 100 | 100 |
| CRUDE 1 mg/ml | 367 | 296 | 23.2 | 0.47 |
| AV 86 100 ug/ml | 569 | 27052 | 36.1 | 43.2 |
| 10 ug/ml | 755 | 25025 | 47.9 | 40 |
| 1 ug/ml | 843 | 26989 | 53.4 | 43.1 |
| 0.1 ug/ml | 421 | 15482 | 26.7 | 24.7 |
| 0.01 ug/ml | 526 | 16304 | 33.3 | 26 |
| 0.001 ug/ml | 270 | 3097 | 17.1 | 4.9 |

TABLE 10

| Concentration of AV 87 | Cpm control | Cpm Con A | No Con A (% of control) | Con A (% of control) |
|---|---|---|---|---|
| CONTROL | 1502 | 50842 | 100 | 100 |
| CRUDE 1 mg/ml | 336 | 273 | 22.3 | 0.53 |
| AV 87 ug/ml | 595 | 39682 | 39.6 | 78 |
| 10 ug/ml | 668 | 25463 | 44.4 | 50 |
| 1 ug/ml | 399 | 12297 | 26.5 | 24.1 |
| 0.1 ug/ml | 142 | 240 | 9.4 | 0.47 |
| 0.01 ug/ml | 306 | 14795 | 20.3 | 29.1 |
| 0.001 ug/ml | 491 | 13872 | 32.6 | 27.2 |

In vitro testing with these compounds clearly shows and inhibitory effect on splenocyte proliferation at doses ranging between 1 pg/ml and 100 ng/ml, and above.

A similar effect was shown with exposure of PHA (phytohemagglutinin)-treated human PMBC cells with AV 74, AV 75, AV 76, a These experiments were performed as the splenocyte experiments. The results show a marked inhibitory effect of AV 75 and AV 77, reaching the maximum of inhibition at concentrations of 100 and 10 mg/ml and exhibiting a dose related inhibition at lower concentrations.

Figure 11:
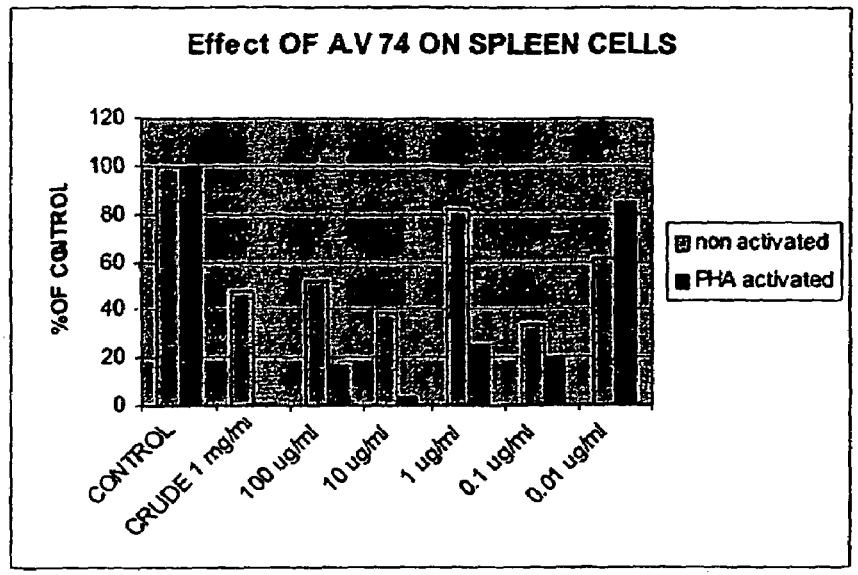
FIG. 11 is a bar graph depicting the effect of AV 75 on spleen cells±PHA.
Figure 12:
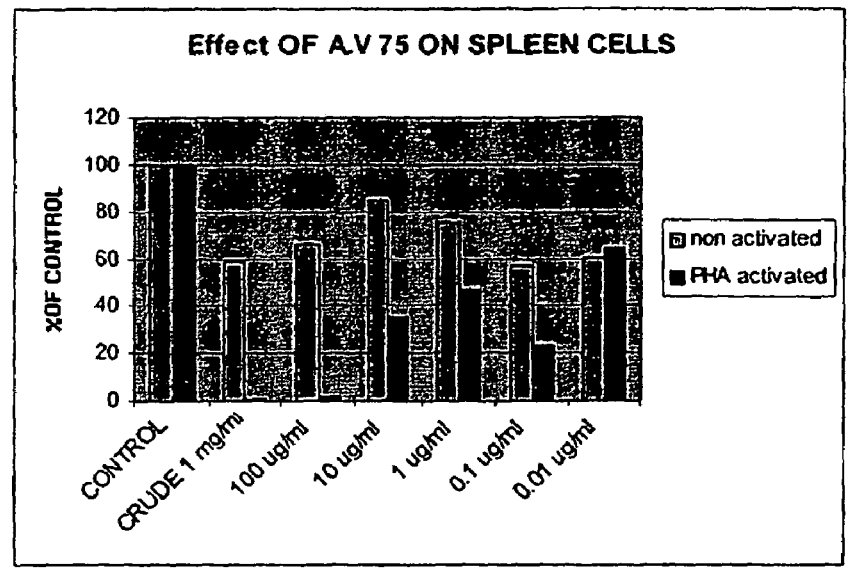
FIG. 12 is a bar graph depicting the effect of AV 75 on spleen cells±PHA.
Figure 13:
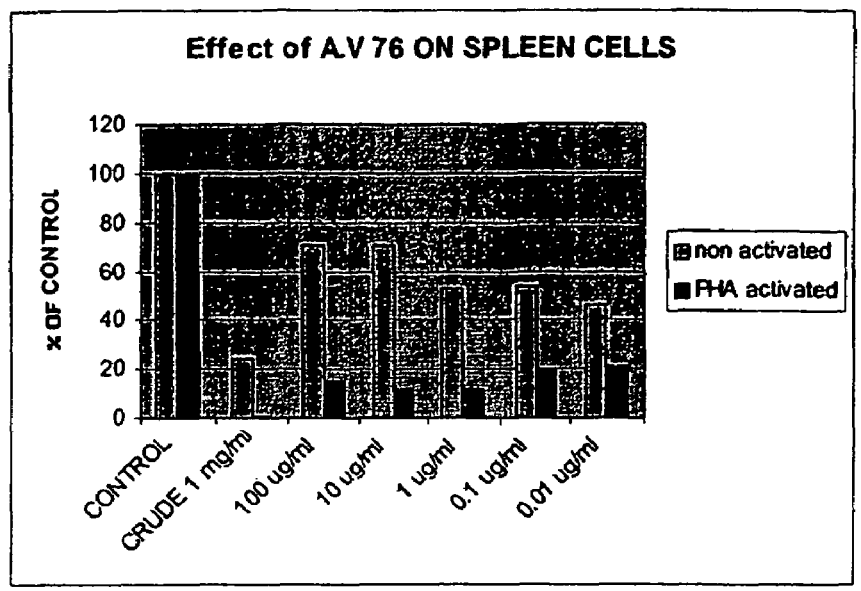
FIG. 13 is a bar graph depicting the effect of AV 76 on spleen cells±PHA.
Figure 14:
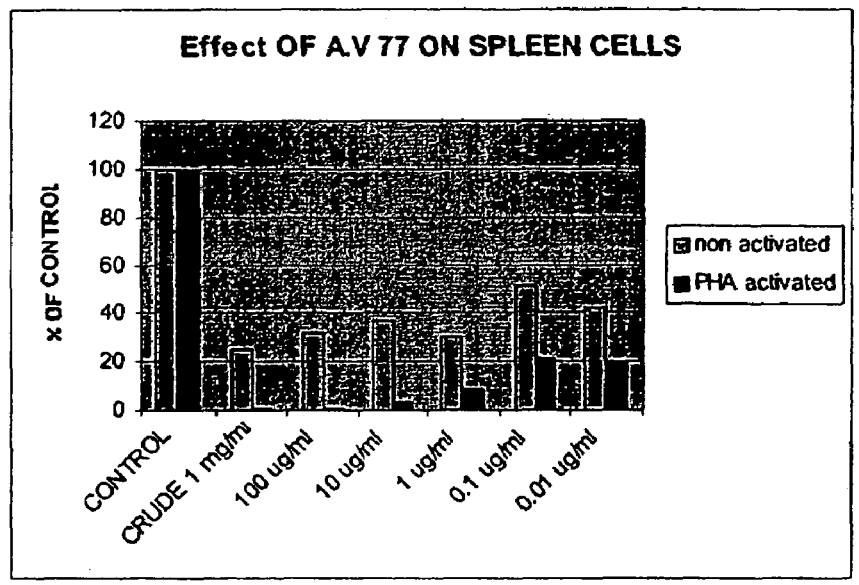
FIG. 14 is a bar graph depicting the effect of AV 77 on spleen cells±PHA.

Data from the AV 74 experiment is shown in Table 11, and summarized in FIG. 11. Data from the AV 75 experiment is shown in Table 12, and summarized in FIG. 12. Data from the AV 76 experiment is shown in Table 13, and summarized in FIG. 13. Data from the AV 77 experiment is shown in Table 14, and summarized in FIG. 14.

TABLE 11

| Concentration of AV 74 | Cpm control | Cpm PHA | No PHA (% of control) | PHA (% of control) |
|---|---|---|---|---|
| CONTROL | 701 | 62309 | 100 | 100 |
| CRUDE 1 mg/ml | 337 | 279 | 48 | 0.44 |
| 100 ug/ml | 363 | 10243 | 51.7 | 16.4 |

TABLE 11-continued

| Concentration of AV 74 | Cpm control | Cpm PHA | No PHA (% of control) | PHA (% of control) |
|---|---|---|---|---|
| 10 ug/ml | 270 | 1972 | 38.5 | 3.16 |
| 1 ug/ml | 575 | 15929 | 82 | 25.5 |
| 0.1 ug/ml | 237 | 12754 | 33.8 | 20.4 |
| 0.01 ug/ml | 431 | 52985 | 61.4 | 85 |

TABLE 12

| Concentration of AV 75 | Cpm control | Cpm PHA | No PHA (% of control) | PHA (% of control) |
|---|---|---|---|---|
| CONTROL | 464 | 49186 | 100 | 100 |
| CRUDE 1 mg/ml | 272 | 360 | 58.6 | 0.73 |
| 100 ug/ml | 309 | 781 | 66.5 | 1.58 |
| 10 ug/ml | 394 | 17516 | 84.9 | 35.6 |
| 1 ug/ml | 352 | 23037 | 75.8 | 46.8 |
| 0.1 ug/ml | 266 | 11662 | 57.3 | 23.7 |
| 0.01 ug/ml | 279 | 31628 | 60.1 | 64.3 |

TABLE 13

| Concentration of AV 76 | Cpm control | Cpm PHA | No PHA (% of control) | PHA (% of control) |
|---|---|---|---|---|
| CONTROL | 446 | 53071 | 100 | 100 |
| CRUDE 1 mg/ml | 109 | 282 | 24.4 | 0.53 |
| 100 ug/ml | 315 | 8233 | 70.6 | 15.5 |
| 10 ug/ml | 316 | 6305 | 70.8 | 11.8 |
| 1 ug/ml | 237 | 6084 | 53.1 | 11.4 |
| 0.1 ug/ml | 238 | 10634 | 53.3 | 20 |
| 0.01 ug/ml | 207 | 11101 | 46.4 | 20.9 |

TABLE 14

| Concentration of AV 77 | Cpm control | Cpm PHA | No PHA (% of control) | PHA (% of control) |
|---|---|---|---|---|
| CONTROL | 405 | 54667 | 100 | 100 |
| CRUDE 1 mg/ml | 103 | 352 | 25.4 | 0.64 |
| 100 ug/ml | 128 | 602 | 31.6 | 1.1 |
| 10 ug/ml | 151 | 1672 | 37.2 | 3 |
| 1 ug/ml | 123 | 4456 | 30.3 | 8.15 |
| 0.1 ug/ml | 209 | 11424 | 51.6 | 20.89 |
| 0.01 ug/ml | 169 | 10518 | 41.7 | 19.24 |

Example 4

Effect of Compounds on Proliferation of T cells

T cells were isolated from buffy coats (BC) of consenting normal human donors (Hadassah Hospital Blood Bank). The BC preparations were diluted 1:4 with phosphate-buffered saline (PBS) that contained 10 U/mL heparin. Peripheral blood mononuclear cells were separated by Ficoll/Paque density centrifugation. Monocytes and B cells were depleted by plastic adherence and passage through nylon wool columns, respectively. Small T lymphocytes were harvested from the pellet of a discontinuous Percoll gradient. The cells were found to be >80% CD3+ by FACS analysis. Cells were cultured in the presence of various concentrations of compound and/or phytohemaglutinin (PHA) (1 μg/ml) T cell mitogen. Proliferation was measured by culturing $1 \times 10^5$ cells in each well of a 96-well flat-bottomed microtiter plates. 48 hrs and 7 days following addition of compound, 1 μCi $^3$[H] thymidine was added to each well and the cultures were incubated for an additional 24 hrs. Samples were harvested and incorporated radioactivity was measured. A 7 day incubation with compounds led to a significant increase in the proliferation of PHA-stimulated T cells versus PHA alone.

Figure 15:
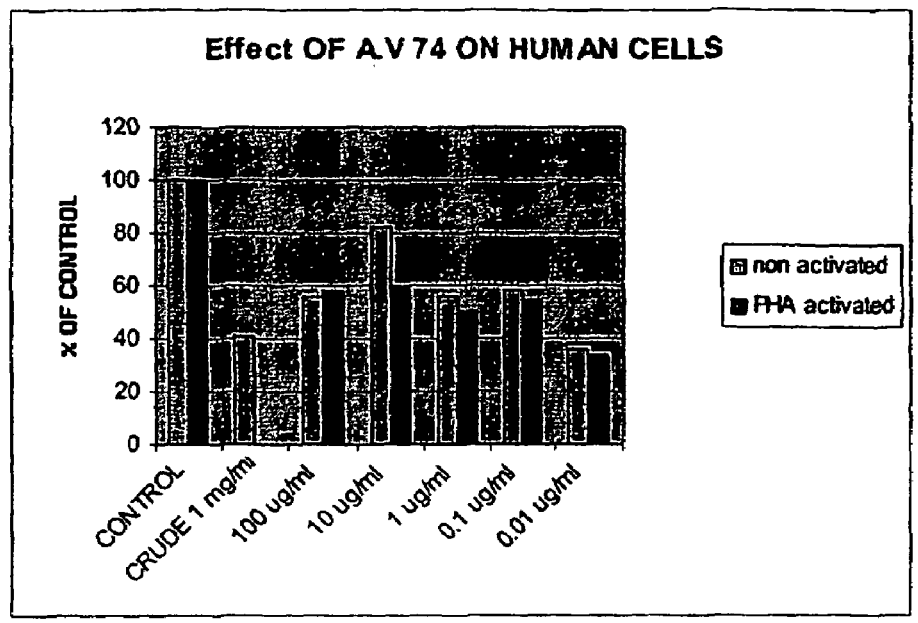
FIG. 15 is a bar graph depicting the effect of AV 74 on PMBCs±PHA.
Figure 16:
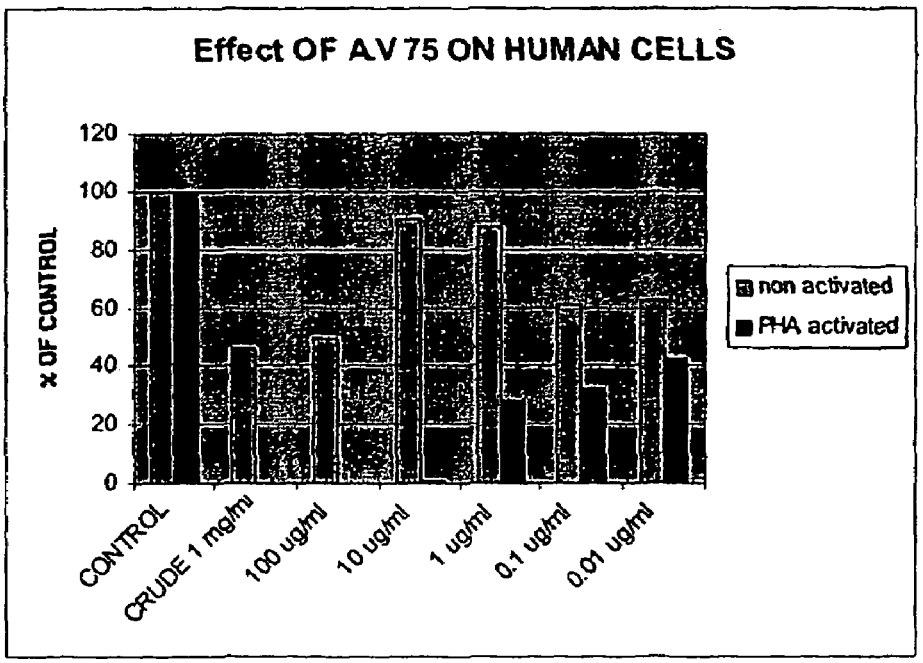
FIG. 16 is a bar graph depicting the effect of AV 75 on PMBCs±PHA
Figure 17:
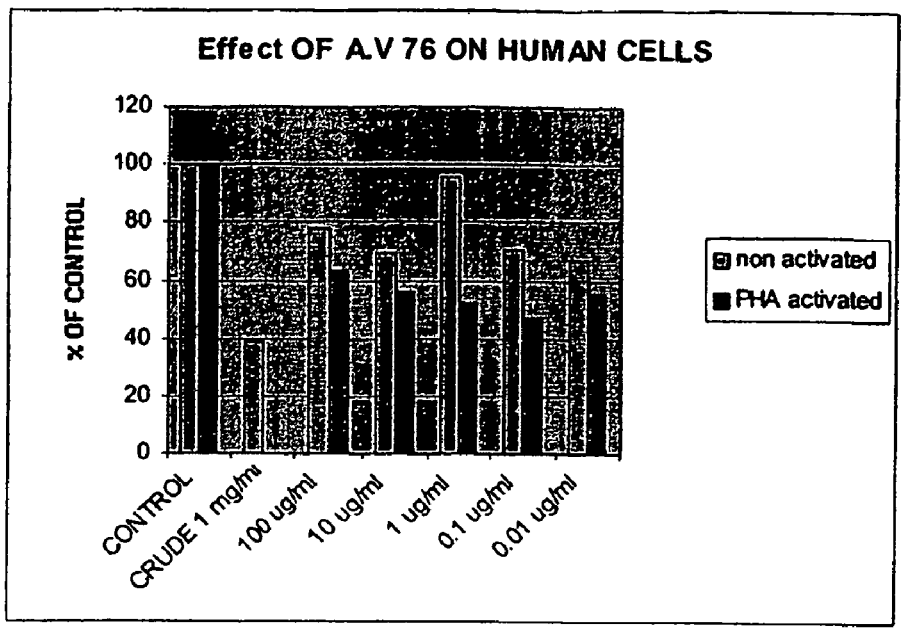
FIG. 17 is a bar graph depicting the effect of AV 76 on PMBCs±PHA.
Figure 18:
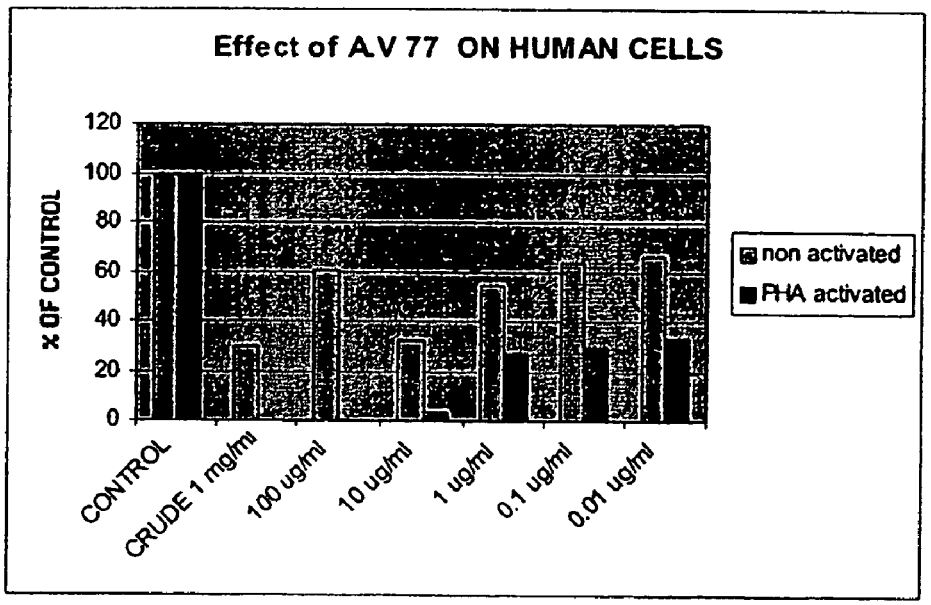
FIG. 18 is a bar graph depicting the effect of AV 77 on PMBCs±PHA.
Figure 19:
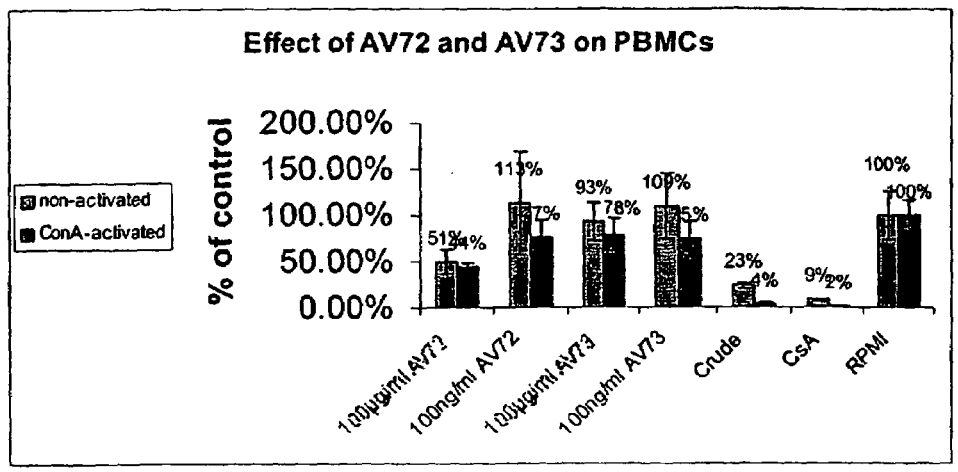
FIG. 19 is a bar graph depicting the effect of AV 72 and AV 73 on PMBCs±ConA relative to those treated with cyclosporin A.
Figure 20:
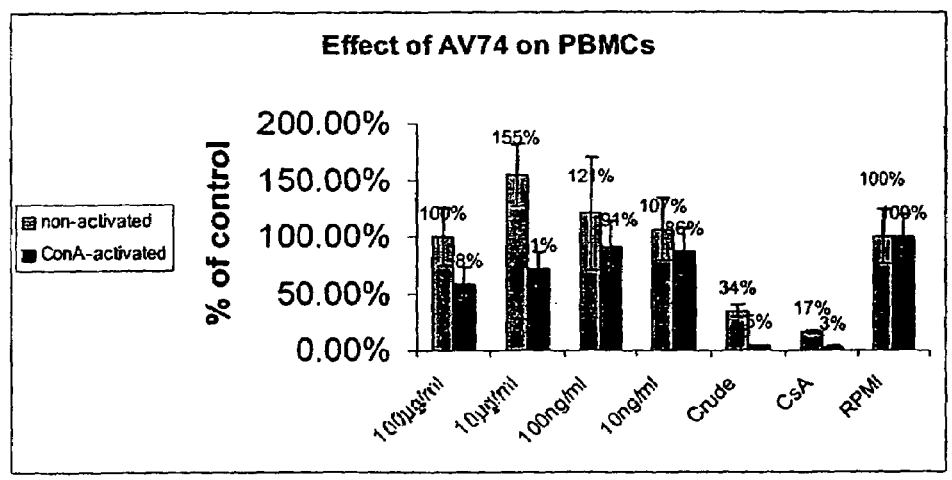
FIG. 20 is a bar graph depicting the effect of AV 74 on PMBCs±ConA relative to those treated with cyclosporin A.
Figure 21:
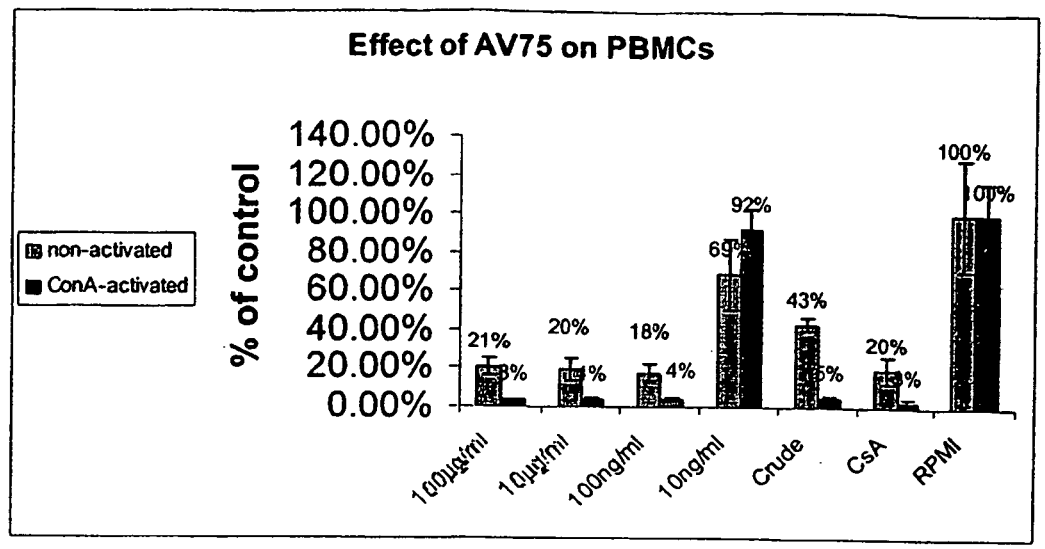
FIG. 21 is a bar graph depicting the effect of AV 75 on PMBCs±ConA relative to those treated with cyclosporin A.
Figure 22:
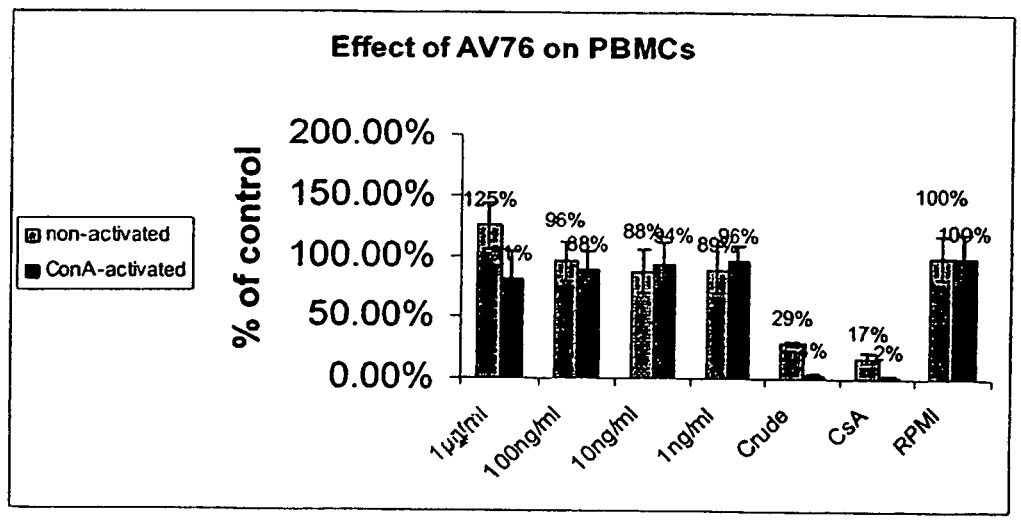
FIG. 22 is a bar graph depicting the effect of AV 76 on PMBCs±ConA relative to those treated with cyclosporin A.
Figure 23:
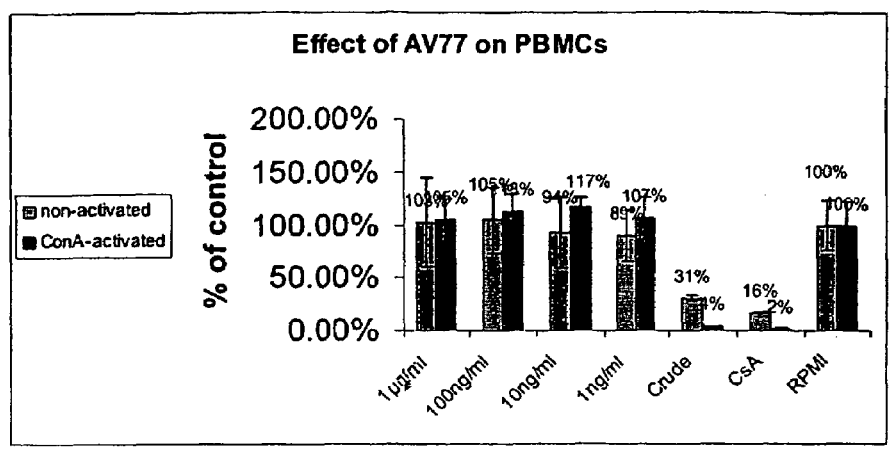
FIG. 23 is a bar graph depicting the effect of AV 77 on PMBCs±ConA relative to those treated with cyclosporin A.

The effect of AV 74, AV 75, AV 76, and AV 77 on PHA (phytohemagglutinin)-treated human peripheral blood mononuclear cells (PMBCs) was investigated. Data from the AV 74 experiment is shown in Table 15, and summarized in FIG. 15. Data from the AV 75 experiment is shown in Table 16, and summarized in FIG. 16. Data from the AV 76 experiment is shown in Table 17, and summarized in FIG. 17. Data from the AV 77 experiment is shown in Table 18, and summarized in FIG. 18.

TABLE 15

| Concentration of AV 74 | Cpm control | Cpm PHA | No PHA (% of control) | PHA (% of control) |
|---|---|---|---|---|
| CONTROL | 620 | 98824 | 100 | 100 |
| CRUDE 1 mg/ml | 254 | 374 | 40.9 | 0.37 |
| 100 ug/ml | 347 | 57433 | 55.9 | 58.1 |
| 10 ug/ml | 513 | 58806 | 82.7 | 59.5 |
| 1 ug/ml | 348 | 49615 | 56.1 | 50.2 |
| 0.1 ug/ml | 365 | 53942 | 58.8 | 54.5 |
| 0.01 ug/ml | 224 | 33259 | 36.1 | 33.65 |

TABLE 16

| Concentration of AV 75 | Cpm control | Cpm PHA | No PHA (% of control) | PHA (% of control) |
|---|---|---|---|---|
| CONTROL | 341 | 99119 | 100 | 100 |
| CRUDE 1 mg/ml | 156 | 295 | 45.7 | 0.29 |
| 100 ug/ml | 170 | 229 | 49.8 | 0.23 |
| 10 ug/ml | 309 | 508 | 90.6 | 0.51 |
| 1 ug/ml | 298 | 27972 | 87.4 | 28.22 |
| 0.1 ug/ml | 209 | 32316 | 61.3 | 32.6 |
| 0.01 ug/ml | 226 | 42178 | 62.2 | 42.55 |

TABLE 17

| Concentration of AV 76 | Cpm control | Cpm PHA | No PHA (% of control) | PHA (% of control) |
|---|---|---|---|---|
| CONTROL | 483 | 105437 | 100 | 100 |
| CRUDE 1 mg/ml | 189 | 339 | 39.1 | 0.32 |
| 100 ug/ml | 376 | 67065 | 77.8 | 63.6 |
| 10 ug/ml | 334 | 58839 | 69.1 | 55.8 |
| 1 ug/ml | 463 | 55382 | 95.8 | 52.52 |
| 0.1 ug/ml | 342 | 49430 | 70.8 | 46.8 |
| 0.01 ug/ml | 323 | 58054 | 66.8 | 55 |

TABLE 18

| Concentration of AV 77 | Cpm control | Cpm PHA | No PHA (% of control) | PHA (% of control) |
|---|---|---|---|---|
| CONTROL | 427 | 95743 | 100 | 100 |
| CRUDE 1 mg/ml | 126 | 351 | 29.5 | 0.36 |
| 100 ug/ml | 259 | 283 | 60.6 | 0.29 |
| 10 ug/ml | 137 | 3593 | 32 | 3.75 |
| 1 ug/ml | 234 | 26456 | 54.8 | 27.6 |

TABLE 18-continued

| Concentration of AV 77 | Cpm control | Cpm PHA | No PHA (% of control) | PHA (% of control) |
|---|---|---|---|---|
| 0.1 ug/ml | 272 | 28229 | 63.7 | 29.48 |
| 0.01 ug/ml | 284 | 31422 | 66.5 | 32.8 |

Example 5

Immunosuppressive Effect of Compounds

Figure 24:
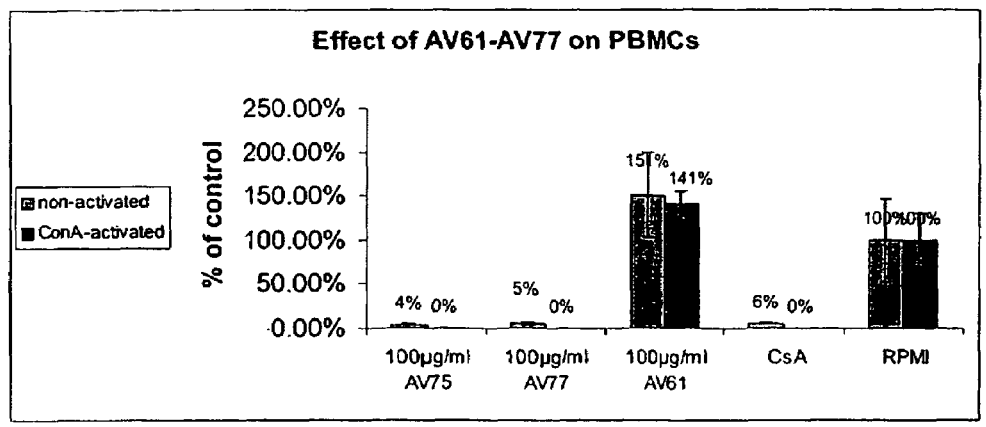
FIG. 24 is a bar graph depicting the effect of AV 61, AV75, and AV 77 on PMBCs±ConA relative, to those treated with cyclosporin A.

Human T cells were isolated as described above. The immunosuppressive effect of AV 72, AV 72, AV 74, AV 75, AV 76, AND AV 77 on PMBCs (both non-activated and ConA-activated) relative to cells treated with CsA (cyclosporin A) is shown in FIGS. 19, 20, 21, 22, and 23, respectively. The effect of AV 61, relative to AV 75 and AV 77 is shown in FIG. 24. The results dearly show the immunosuppressive effect of AV 75 and AV 77 on PBMCs, reaching the maximal suppressive effect with 100 ng/ml with AV 75 and 100 pg/ml with AV 77.

Figure 25:
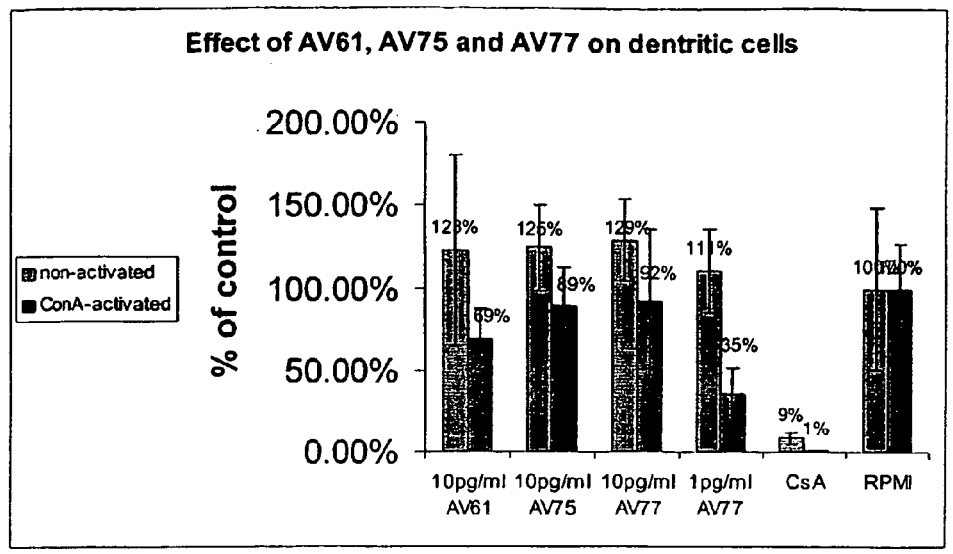
FIG. 25 is a bar graph depicting the effect of AV 61, AV75, and AV 77 on dendritic cells±ConA relative to those treated with cyclosporin A.

The immunosuppressive effect of AV 61, AV 75, and AV 77 on dendritic cells (both non-activated and ConA-activated) relative to cells treated with CsA (cyclosporin A) is shown in FIG. 25. Thus, the suppressive effect of AV 77 was shown not only on the PBMCs but also on antigen presenting cells (APCs) such as dentritic cells, reaching a suppressive effect of 65% with 1 pg/ml).

Example 6

Effect of AV 75 on Experimental AutoImmune Encephalomyelitis

Experimental autoimmune encephalomyelitis (EAE) is an organ-specific T cell-mediated autoimmune disease resulting in demyelination of the white matter in the central nervous system (CNS). In many of its clinical and histopathological aspects, EAE resembles human multiple sclerosis (MS) and acute disseminating encephalomyelitis. Early histopathological manifestations of the disease are infiltrating monocytic lesions followed by infiltrating lymphocytic ones in the brain and spinal cord, with areas of demyelination in the white matter of the CNS. The ability of AV 75 to abrogate pathogenesis of acute EAE was investigated.

Animals:

Twenty-four female SJL/J mice, 6-12 week old were used for this experiment. They were housed under standard conditions in top filtered cages, and were fed a regular diet without antibiotics.

Induction and Clinical Evaluation of EAE:

Induction of acute EAE in SJL mice was based on a modification of Bernard's procedure (Bernard et al., J. Immunol. 114, 1537-1540 (1975)). Briefly, equal volumes of Mouse Spinal Cord Homogenate (MSCH) 100 mg/ml in PBS and CFA enriched with *Mycobacterium tuberculosis* H37Ra (6 mg/ml) were emulsified. The emulsion (50-100 µl) was administered subcutaneously into the four footpads of each mouse. Immediately thereafter, and 2 days later, mice were injected i.v. with pertussigen. All animals were examined daily for signs of disease. The first clinical indication appeared on day 11-12 post immunization and were scored according to the following six point scale: 0, no abnormality; 1, mild tail weakness; 2, tail paralysis; 3, tail paralysis and hind leg paresis; 4, hind leg paralysis or mild forelimb weakness; 5, quadriplegia or moribund state; 6, death.

AV 75 Treatment:

Av 75 was administered intraperitoneally at two dose levels of 1 µg and 100 µg per animal, 3 times a week for the duration of the experiment. The administration was initiated on day 0, immediately following the immunization with MSCH for the induction of EAE. AV 75 administered as 100 pg/ml in drinking water of mice (ad libitum), changing the water twice a week has also resulted in positive results in the acute EAE model of MS.

In vitro Proliferative Responses of Lymphocytes:

Draining lymph nodes were excised from EAE and control mice at day 10 after immunization. Single cell suspensions of lymphocytes were assayed by [$^3$H]thymidine incorporation. The assay was carried out by seeding $4 \times 10^5$ cells/well in 0.2 ml of RPMI medium supplemented with 2.5% fetal calf serum, L-glutamine, antibiotics and optimal concentrations of the following antigens: PLP (proteolipid protein, a myelin peptide), PPD (tuberculin-purified protein derivative), ConA (concanavalin A), SEB (*Staphylococcal* enterotoxin B) MOG (myelin oligodendrocytes glycoprotein) and LPS (lipopolysaccharide).

Results:

The 24 mice were divided in 3 groups: 8 mice served as control; 8 mice received 1 µg per animal and 8 mice received 100 µg per animal on each injection, three times a week during the experiment. On day 10, two mice from each group were sacrificed and their draining lymph nodes were excised with the aim to be assayed in the in vitro proliferation assay for response to antigens.

Figure 26:
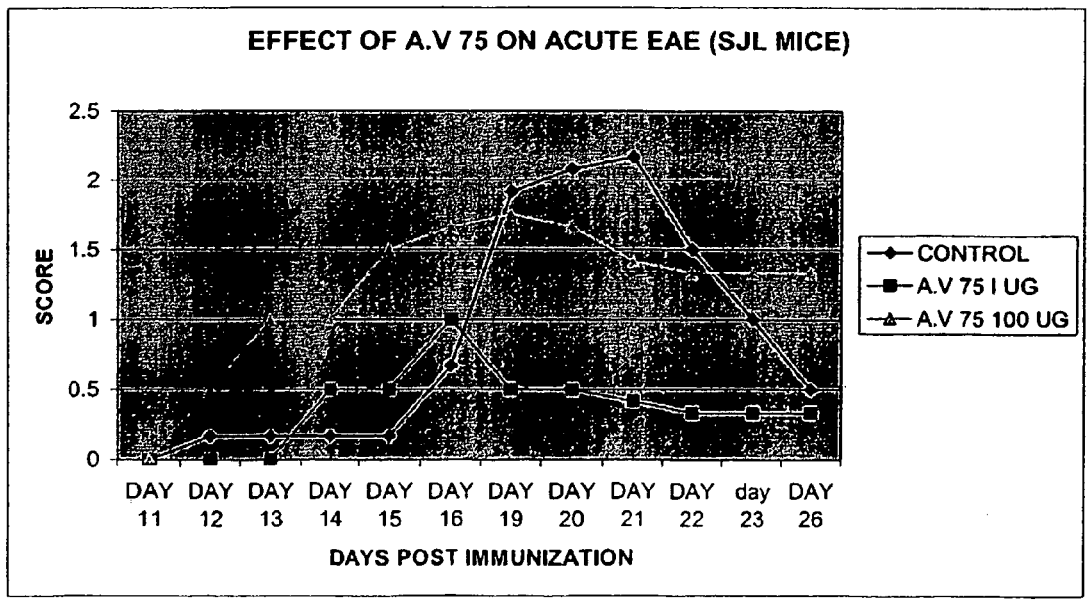
FIGS. 26A, B, and C are line graphs depicting the effect of AV 75 on experimental autoimmune encephalomyelitis. The pathological score is recorded as a function of days after treatment.
Figure 26:
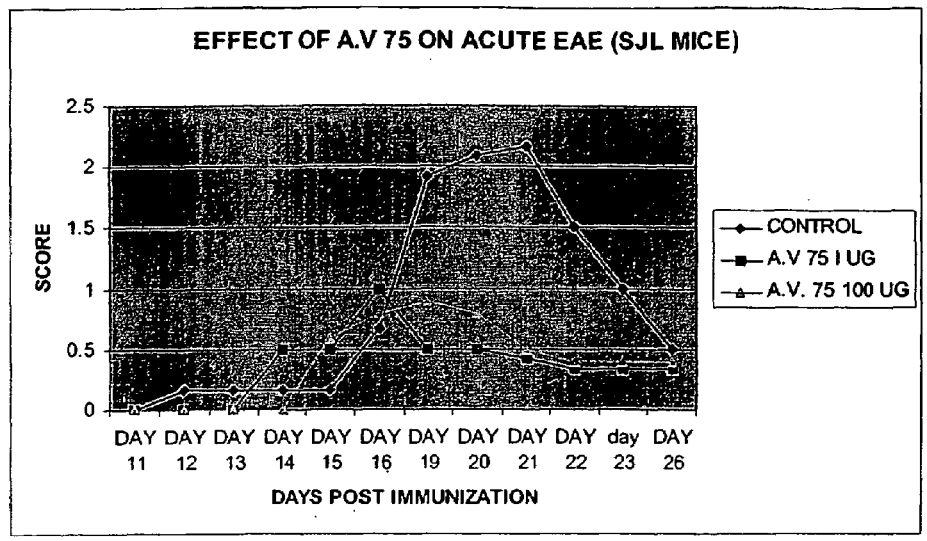
Figure 26:
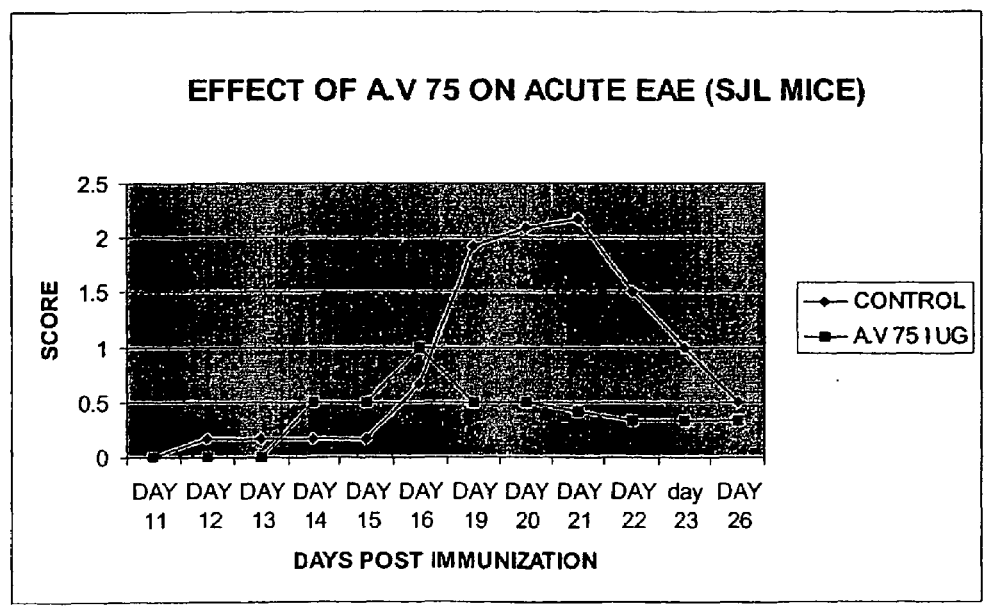

The remaining 6 animals per group continued with the experiment. One animal in the 100 µg group died for unknown reasons. The results of the experiment are presented in FIGS. 26A, B, and C: the control group developed the disease as expected. Only 2 animals in each AV 75 treated group developed relatively mild signs of the disease, and in the graph the differences between the treated and untreated groups can be clearly seen.

Figure 27A:
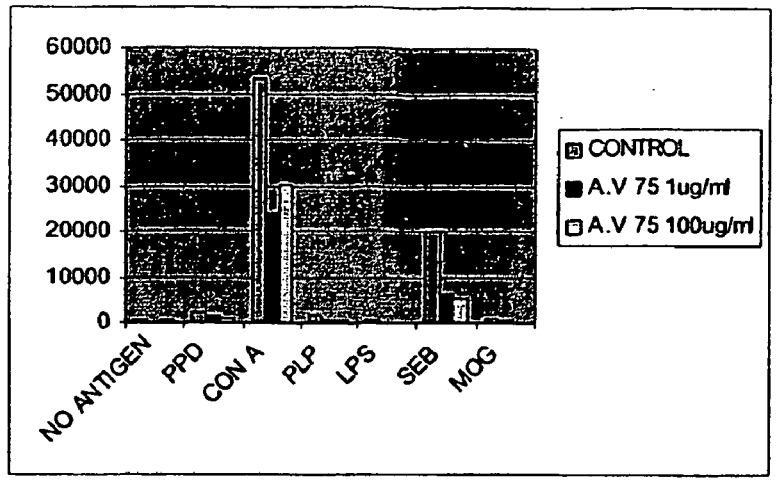
FIG. 27A is a bar graph summarizing the effect of AV 75 on the proliferative response to a variety of antigens by lymphocytes obtained from mouse lymph nodes.
Figure 27:
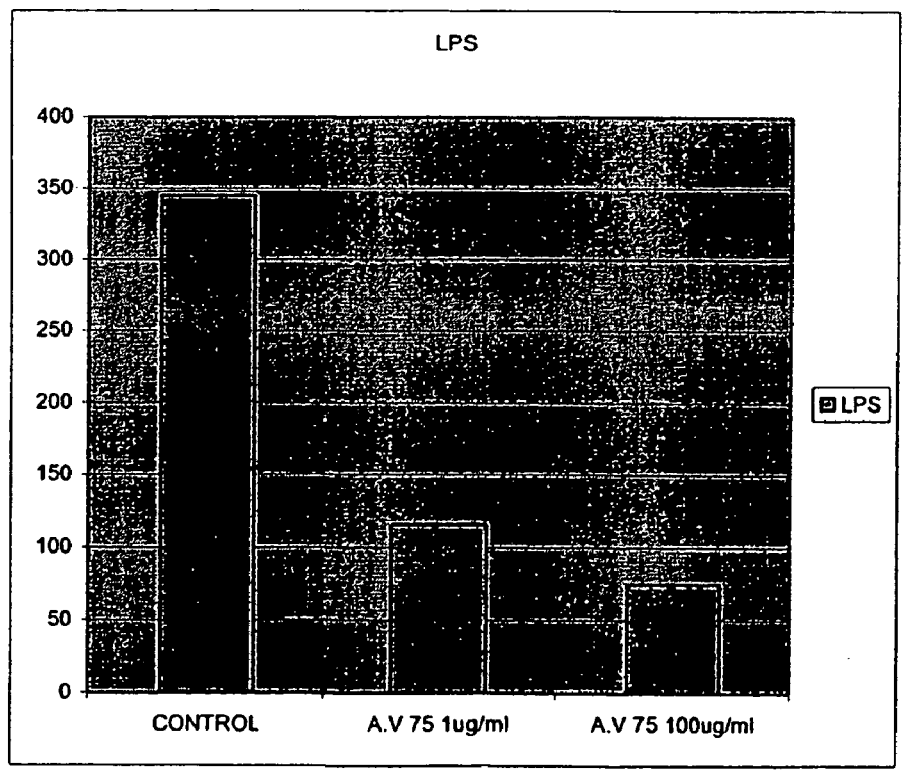
FIG. 27B depicts the effect of AV 75 on the proliferative response to LPS by lymphocytes obtained from mouse lymph nodes.
FIG. 27C depicts the effect of AV 75 on the proliferative response to SEB by lymphocytes obtained from mouse lymph nodes.
FIG. 27D depicts the effect of AV 75 on the proliferative response to ConA by lymphocytes obtained from mouse lymph nodes.
FIG. 27E depicts the effect of AV 75 on the proliferative response to PPD by lymphocytes obtained from mouse lymph nodes.
FIG. 27F depicts the effect of AV 75 on the proliferative response to PLP by lymphocytes obtained from mouse lymph nodes.
FIG. 27G depicts the effect of AV 75 on the proliferative response to control treated lymphocytes obtained from mouse lymph nodes.
Figure 27:
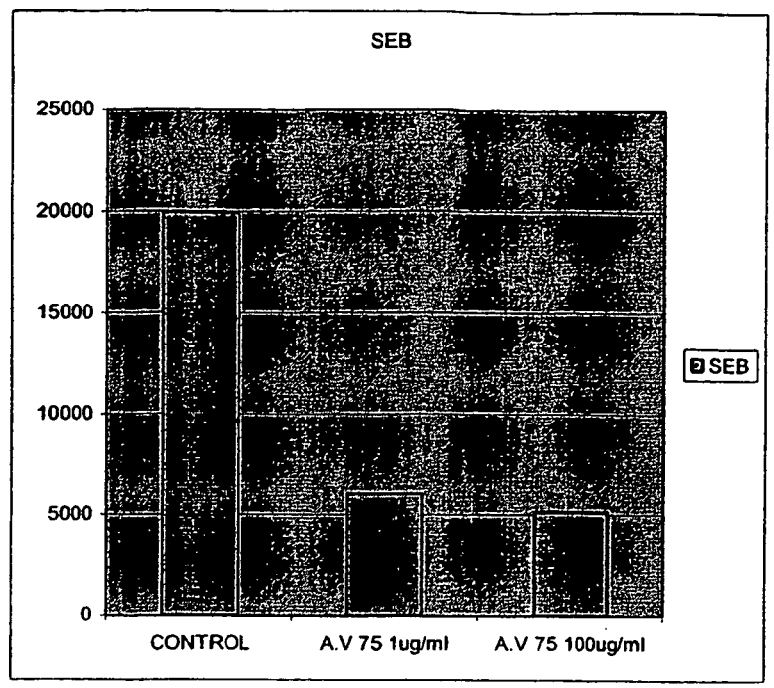
Figure 27:
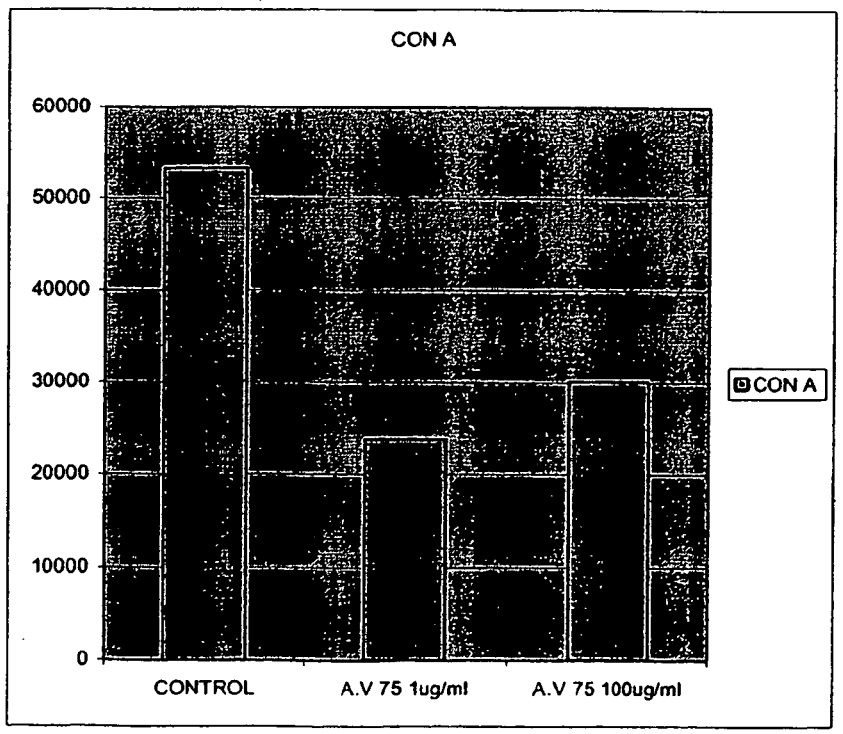
Figure 27:
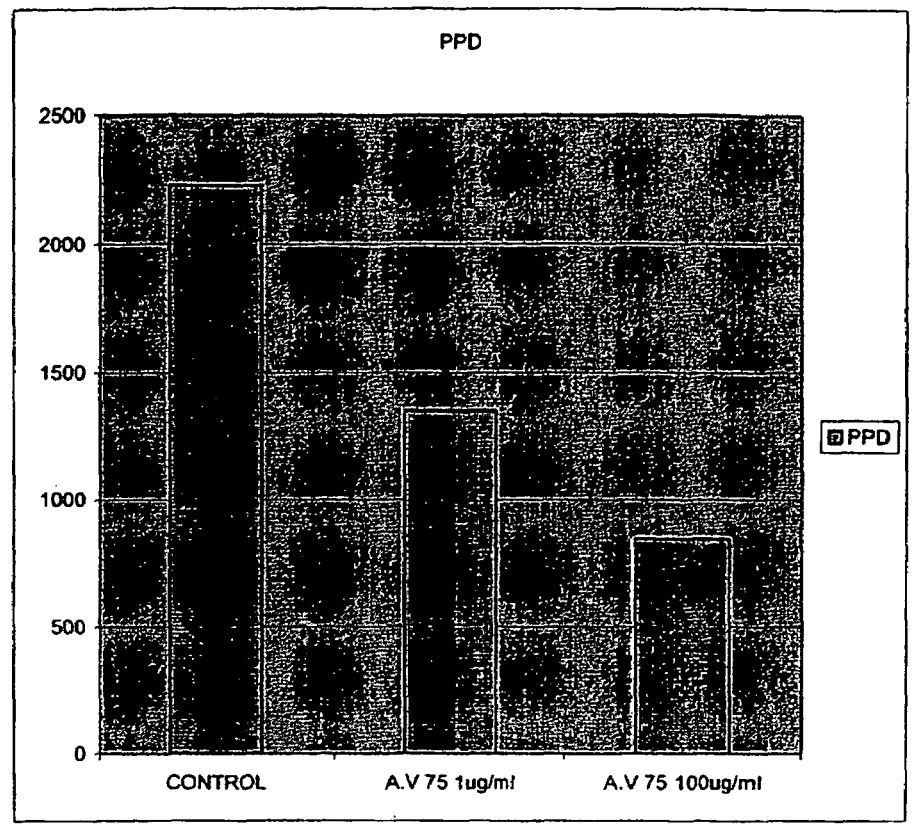
Figure 27:
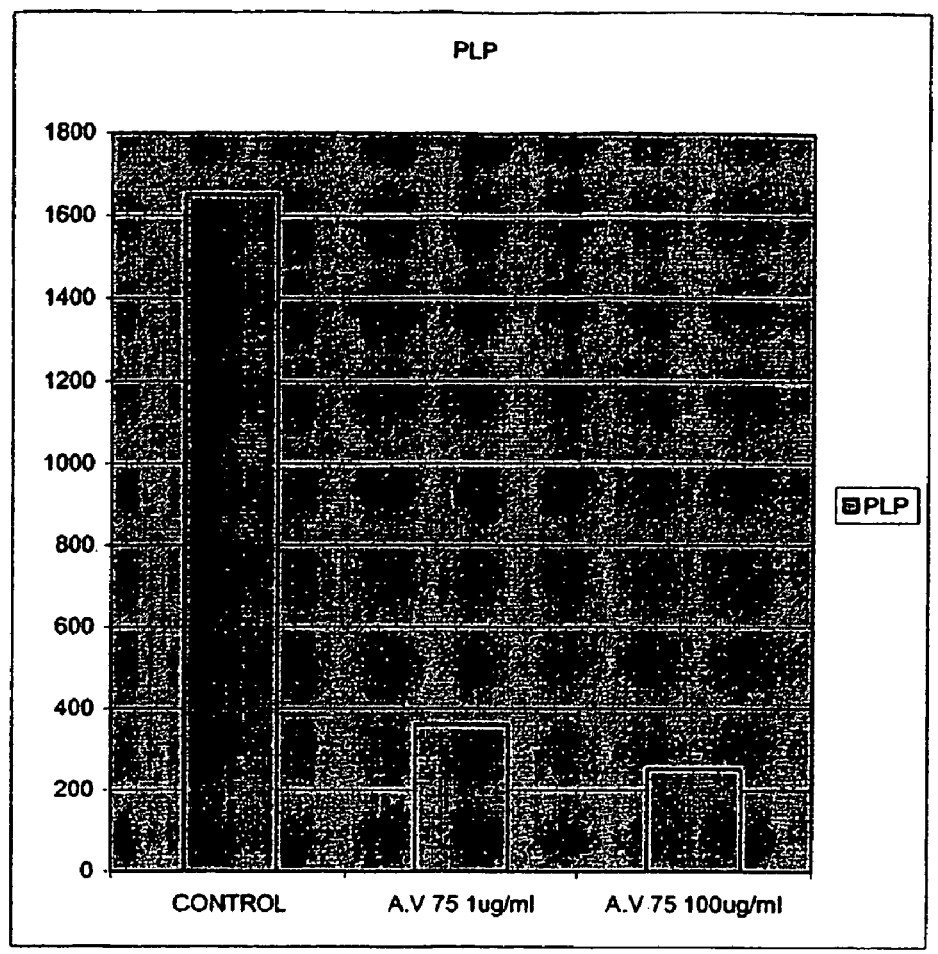
Figure 27:
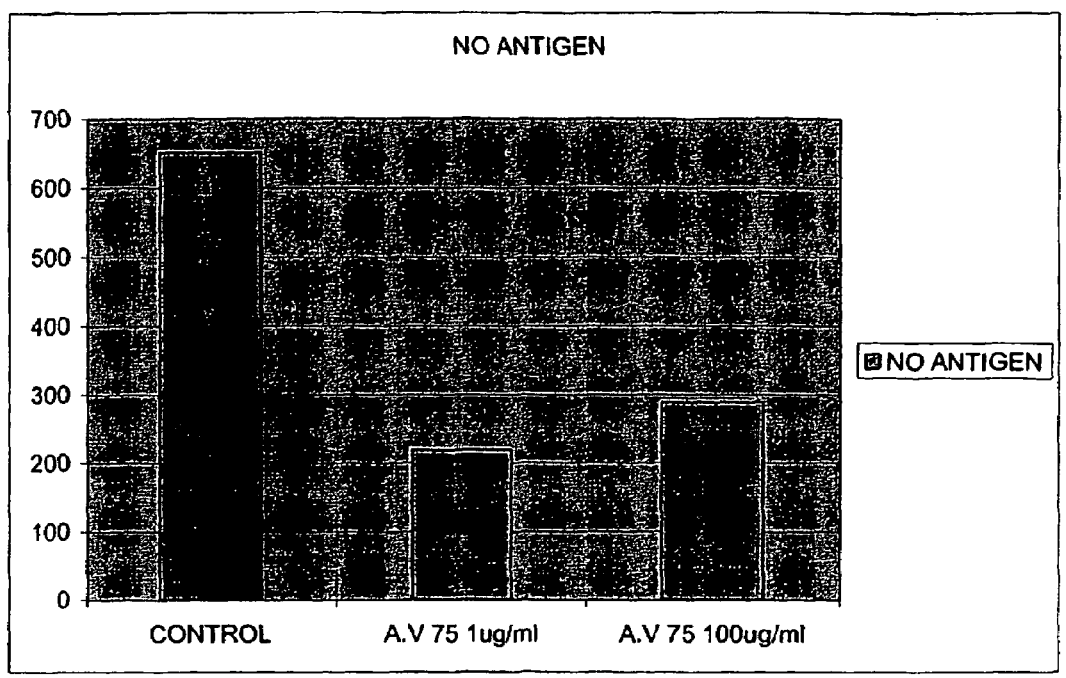

The results of the proliferative response to antigens of the lymphocytes obtained from the draining lymph nodes are summarized in FIG. 27A. Data from individual antigen experiments is presented in FIGS. 27B-F. Data from the control (no antigen) experiment is shown in FIG. 27G. These results represent the average of the 2 lymph nodes from each group. The inhibitory effect of the 2 doses of AV 75 against all the antigens tested is evident. Especially remarkable is the effect against the PLP antigen, the most distinctive antigen in EAE.

Example 7

Effect of AV 75 and AV 77 on Transplant Rejection

The effect of AV 75 and AV 77 transplant rejection was investigated in vivo in a rat acute renal allograft rejection model. Kidneys from Brown-Norway rats (donors) were orthotopically transplanted into Lewis rats (recipients), followed by right nephrectomy of the recipients. In the group receiving two injections of 100 ng per rat of AV 75, on days 0 and 4 after transplantation, prevention of the rejection has been observed for long periods (e.g., up to 53 days as compared to up to 4 days survival of the controls). Data is summarized in Table 19.

TABLE 19

| Treatment | Subject | Compound | Survival time |
|---|---|---|---|
| transplantation and compound (100 ug) | TAA1 | AV75 | 2 days |
| | TAA2 | AV75 | 4 days |
| | TAA3 | AV75 | 4 days |
| | TAB1 | AV77 | 3 days |
| | TAB2 | AV77 | 3 days |
| | TAB3 | AV77 | 2 days |
| | TAC1 | vehicle | 3 days |
| | TAC2 | vehicle | 2 days |
| | TAD1 | AV75 | 3 days |
| | TAD2 | AV75 | 3 days |
| | TAD3 | AV75 | 2 days |
| | TAE1 | AV77 | 3 days |
| | TAE2 | AV77 | 3 days |
| | TAE3 | AV77 | 2 days |
| | TAF1 | vehicle | 3 days |
| | TAF2 | vehicle | 3 days |
| transplantation and compound (100 ng) | TAA1 | AV75 | 4 days |
| | TAA2 | AV75 | 6 days |
| | TAA3 | AV75 | 5 days |
| | TAB1 | AV77 | 4 days |
| | TAB2 | AV77 | 4 days |
| | TAB3 | AV77 | 2 days |
| | TAB4 | AV77 | 4 days |
| | TAC1 | vehicle | 3 days |
| | TAC2 | vehicle | 4 days |
| | TAC3 | vehicle | 3 days |
| | TAC4 | vehicle | 3 days |
| | TAD1 | AV75 | 53 days |
| | TAD2 | AV75 | 5 days |
| | TAD3 | AV75 | 35 days |
| | TAD4 | AV75 | 34 days |
| | TAE1 | AV77 | 3 days |
| | TAE2 | AV77 | 4 days |
| | TAE3 | AV77 | 3 days |
| | TAE4 | AV77 | 5 days |
| | TAF1 | vehicle | 4 days |
| | TAF2 | vehicle | 4 days |
| | TAF3 | vehicle | 3 days |
| | TAF4 | vehicle | 3 days |
| transplantation and compound (100 pg) | TAA1 | AV75 | 4 days |
| | TAA2 | AV75 | 6 days |
| | TAA3 | AV75 | 7 days |
| | TAA4 | AV75 | 6 days |
| | TAB1 | AV77 | 3 days |
| | TAB2 | AV77 | 4 days |
| | TAB3 | AV77 | 6 days |
| | TAC1 | vehicle | 3 days |
| | TAC2 | vehicle | 3 days |
| | TAC3 | vehicle | 3 days |
| | TAD1 | AV75 | 3 days |
| | TAD2 | AV75 | 10 days |
| | TAD3 | AV75 | 8 days |
| | TAE1 | AV77 | 5 days |
| | TAE2 | AV77 | 4 days |
| | TAE3 | AV77 | 5 days |
| | TAF1 | vehicle | 3 days |
| | TAF2 | vehicle | 4 days |
| | TAF3 | vehicle | 3 days |
| transplantation and compound (100 pg) i.p. day 0 and day 3 | TAN1 | AV75 | 6 days |
| | TAN2 | AV75 | 5 days |
| | TAN3 | AV75 | 6 days |
| | TAN4 | AV75 | 7 days |
| | TAN5 | AV75 | 6 days |
| | TAN6 | AV75 | 5 days |
| transplantation and compound (100 ng) i.p. day 0 and day 3 | TAG1 | AV75 | 3 days |
| | TAG2 | AV75 | 4 days |
| | TAG3 | AV75 | 3 days |
| | TAG4 | AV75 | 3 days |
| | TAG5 | AV75 | 4 days |
| transplantation and compound (100 ng) i.p. day −1 and day 3 | TAH1 | AV75 | 4 days |
| | TAH2 | AV75 | 3 days |
| | TAH3 | AV75 | 4 days |
| | TAH4 | AV75 | 3 days |
| transplantation and compound (100 ng) i.p. day 0 and day 4 | TAI1 | AV75 | 4 days |
| transplantation and compound (100 ng) i.p. day −1 and day 3 | TAJ1 | AV75 | 3 days |

It will be appreciated that the present invention is not limited by what has been described hereinabove and that numerous modifications, all of which fall within the scope of the present invention, exist. Rather the scope of the invention is defined by the claims that follow.

What is claimed is:

1. A compound of formula I:

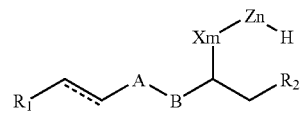

wherein:

the dotted line represents a single or a double bond;

$R_1$ and $R_2$ are the same or different and, independently of each other, are groups represented by the formula:

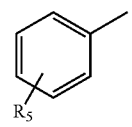

in which $R_5$ is H, OH or $OR_6$, where $R_6$ is a linear or branched $C_1$-$C_4$ alkyl;

A-B is a group represented by the formula:

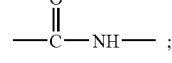

and

X is, —$CH_2O$—, —$CH_2CH_2O$—, —$CH(CH_3)CH_2O$— or —$CH_2CH(CH_3)O$—;

Z is —$CH_2CH_2O$—, —$CH(CH_3)CH_2O$— or —$CH_2CH(CH_3)O$—;

m is 1, and n is an integer of 1-50 and salts thereof.

2. The compound of claim 1, wherein $R_1$ is:

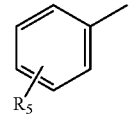

where $R_5$ is H or OH.

3. The compound of claim 2, wherein $R_1$ is phenyl.

4. The compound of claim 2, wherein $R_1$ is:

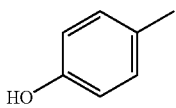

5. The compound of claim 1, wherein $R_2$ is:

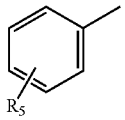

wherein $R_5$ is H or OH.

6. The compound of claim 5, wherein $R_2$ is phenyl.

7. The compound of claim 5, wherein $R_2$ is

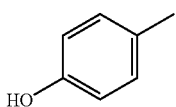

8. The compound of claim 1, wherein X is —$CH_2$O—.

9. The compound of claim 1, wherein Z is —CH($CH_3$)$CH_2$O— or —$CH_2$CH($CH_3$)O—.

10. The compound of claim 8, wherein Z is —CH($CH_3$)$CH_2$O— or —$CH_2$CH($CH_3$)O—.

11. The compound of claim 8, wherein $R_1$ is

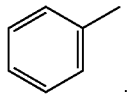

12. The compound of claim 10, wherein $R_1$ is

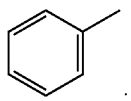

13. The compound of claim 8, wherein $R_1$ is

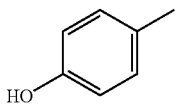

14. The compound of claim 10, wherein $R_1$ is

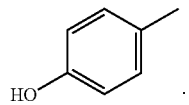

15. The compound of claim 8, wherein $R_2$ is

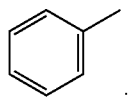

16. The compound of claim 10, wherein $R_2$ is

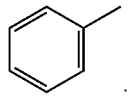

17. The compound of claim 8, wherein $R_2$ is

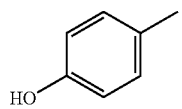

18. The compound of claim 10, wherein $R_2$ is

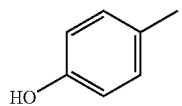

19. The compound of claim 1, wherein n is an integer of 1-20.

20. The compound of claim 8, wherein n is an integer of 1-20.

21. The compound of claim 10, wherein n is an integer of 1-20.

22. The compound of claim 1, wherein n is an integer of 10-20.

23. The compound of claim 8, wherein n is an integer of 10-20.

24. The compound of claim 10, wherein n is an integer of 10-20.

25. The compound of claim 1, wherein n is 7.

26. The compound of claim 8, wherein n is 7.

27. The compound of claim 10, wherein n is 7.

28. The compound of claim 1, wherein n is an integer of 5-50.

29. The compound of claim 8, wherein n is an integer of 5-50.

30. The compound of claim 10, wherein n is an integer of 5-50.

31. A pharmaceutical composition comprising one or more compounds according to claim 1 together with one or more pharmaceutically acceptable excipients or adjuvants.

32. The composition of claim 31, formulated as uncoated tablets, coated tablets, pills, capsules, powder or suspension.

33. The composition of claim 31, formulated in an ointment, cream or gel form.

34. A compound of formula II:

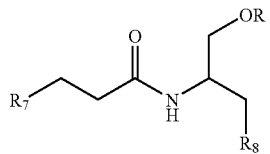

wherein R is a polyalkylene glycol polymer having n units, where n is an integer from 1-50, and $R_7$ and $R_8$ are selected from the combinations shown:

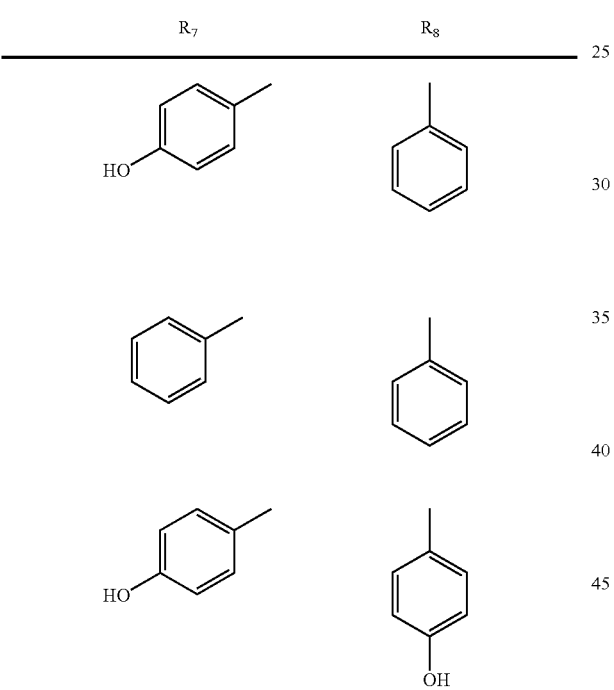

| $R_7$ | $R_8$ |
|---|---|
| 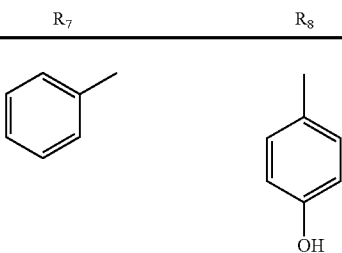 | 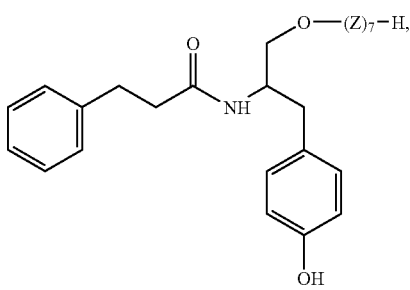 | and salts thereof.

35. A compound of the formula:

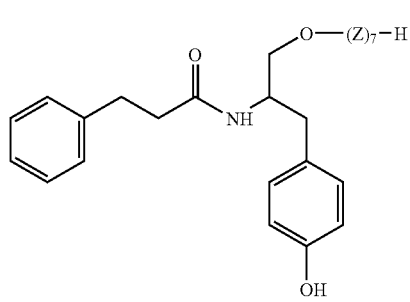

wherein Z is —CH(CH$_3$)CH$_2$O— or —CH$_2$CH(CH$_3$)O—, or salt thereof.

36. A pharmaceutical composition comprising a compound of the formula:

wherein, Z is —CH(CH$_3$)CH$_2$O— or —CH$_2$CH(CH$_3$)O—, together with one or more pharmaceutically acceptable excipients or adjuvants.

* * * * *

UNITED STATES PATENT AND TRADEMARK OFFICE
CERTIFICATE OF CORRECTION

PATENT NO. : 7,642,290 B2 Page 1 of 1
APPLICATION NO. : 10/530116
DATED : January 5, 2010
INVENTOR(S) : Eliahu Kaplan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this

Sixteenth Day of November, 2010

David J. Kappos
*Director of the United States Patent and Trademark Office*